US011096692B2

(12) United States Patent
Rowe et al.

(10) Patent No.: US 11,096,692 B2
(45) Date of Patent: Aug. 24, 2021

(54) BLOOD OXYGENATION TREATMENT METHODS AND DEVICES

(71) Applicant: NXT Biomedical, LLC, Irvine, CA (US)

(72) Inventors: Stanton J. Rowe, Newport Coast, CA (US); Robert S. Schwartz, Inver Grove Heights, MN (US); Glen Rabito, Lake Forest, CA (US); Robert C. Taft, Orange, CA (US); Elliot Howard, Irvine, CA (US); Alexander Siegel, Aliso Viejo, CA (US); Joseph Passman, Costa Mesa, CA (US)

(73) Assignee: NXT Biomedical, LLC, Irvine, CA (US)

( * ) Notice: Subject to any disclaimer, the term of this patent is extended or adjusted under 35 U.S.C. 154(b) by 0 days.

(21) Appl. No.: 16/714,611

(22) Filed: Dec. 13, 2019

(65) Prior Publication Data

US 2020/0187945 A1 Jun. 18, 2020

Related U.S. Application Data

(60) Provisional application No. 62/779,380, filed on Dec. 13, 2018, provisional application No. 62/802,656, (Continued)

(51) Int. Cl.
*A61B 17/11* (2006.01)
*A61B 5/145* (2006.01)
(Continued)

(52) U.S. Cl.
CPC .......... *A61B 17/11* (2013.01); *A61B 5/14542* (2013.01); *A61B 5/686* (2013.01);
(Continued)

(58) Field of Classification Search
CPC ..... A61B 17/11; A61B 5/14542; A61B 5/686; A61B 17/00234; A61B 17/12022; A61B 2017/00252; A61B 2017/1139
(Continued)

(56) References Cited

U.S. PATENT DOCUMENTS

| 5,743,259 A | * | 4/1998 | Kruse | ............... A61B 5/14539 |
| | | | | 600/309 |
| 2004/0193231 A1 | | 9/2004 | David et al. | |

(Continued)

OTHER PUBLICATIONS

WIPO, U.S. International Search Authority, International Search Report and Written Opinion dated Feb. 25, 2020 in International Patent Application No. PCT/US2019/066399, 8 pages.
(Continued)

*Primary Examiner* — Andrew J Mensh
(74) *Attorney, Agent, or Firm* — Inskeep IP Group, Inc.

(57) ABSTRACT

Methods and devices for increasing oxygenation levels in the blood supply and thereby treating the condition of hypoxemia. Multiple approaches such as pressure reduction in the pulmonary circulatory system, reducing triggering mechanisms in the main pulmonary artery and restricting flow in the pulmonary circulatory system are disclosed. Interventions associated with those approaches can including shunting, restrictors, compliance devices, pharmacologic substances, etc.

14 Claims, 24 Drawing Sheets

Related U.S. Application Data filed on Feb. 7, 2019, provisional application No. 62/896,144, filed on Sep. 5, 2019, provisional application No. 62/942,631, filed on Dec. 2, 2019.

(51) Int. Cl.
*A61B 5/00* (2006.01)
*A61B 17/00* (2006.01)
*A61B 17/12* (2006.01)

(52) U.S. Cl.
CPC .. *A61B 17/00234* (2013.01); *A61B 17/12022* (2013.01); *A61B 2017/00252* (2013.01); *A61B 2017/1139* (2013.01)

(58) Field of Classification Search
USPC .............................................. 604/8
See application file for complete search history.

(56) References Cited

U.S. PATENT DOCUMENTS

| | | |
|---|---|---|
| 2004/0249335 A1 | 12/2004 | Faul et al. |
| 2005/0021092 A1* | 1/2005 | Yun .................... A61N 1/36017 607/3 |
| 2014/0018649 A1* | 1/2014 | Jespersen ............. A61B 5/4064 600/322 |
| 2016/0031903 A1 | 2/2016 | Nakai et al. |
| 2017/0182277 A1 | 6/2017 | Niklewski et al. |
| 2018/0153440 A1 | 6/2018 | Lee et al. |
| 2019/0343579 A1 | 11/2019 | Tandri et al. |

OTHER PUBLICATIONS

WIPO, U.S. International Preliminary Examining Authority, International Preliminary Report on Patentability dated Sep. 4, 2020 in International Patent Application No. PCT/US2019/066399, 22 pages.

\* cited by examiner

BLOOD OXYGENATION TREATMENT METHODS AND DEVICES

RELATED APPLICATIONS

This application claims priority to U.S. Provisional Application Ser. No. 62/779,380 filed Dec. 13, 2018 entitled Methods and Technology For Creating Connections and Shunts Between Vessels and Chambers of Biologic Structures and to U.S. Provisional Application No. 62/802,656 filed Feb. 7, 2019 entitled Methods and Technology For Creating Connections and Shunts Between Vessels and Chambers of Biologic Structures and to U.S. Provisional Application Ser. No. 62/896,144 filed Sep. 5, 2019 entitled Rivet Stent) and to U.S. Provisional Application Ser. No. 62/942,631 filed Dec. 2, 2019 entitled Rivet Stent), all of which are hereby incorporated herein by reference in their entireties.

FIELD OF THE INVENTION

The present invention generally relates to devices and methods for improving oxygen levels in the blood of a mammal, and particularly to method and devices for treating hypoxemia in humans.

BACKGROUND OF THE INVENTION

The cardiopulmonary system is critical to supplying the body with adequate oxygen to meet the metabolic demands of the body. Hypoxemia is defined as an abnormally low level of oxygen in the blood. This can lead to clinical problems such as ischemia, sepsis, organ failure, and death.

Methods and devices to safely improve the partial pressure of arterial oxygen ($PaO_2$, mmHg), arterial oxygen saturation ($SaO_2$, %), and/or peripheral oxygen saturation ($SpO_2$, %) without the use of long term oxygen therapy (LTOT) or even supplemental oxygen therapy could substantially improve the quality of life and prognosis of the hundreds of millions of people with hypoxemia[1-3] that are indicated for LTOT or supplemental oxygen world-wide.

LTOT is generally indicated in patients with: An arterial oxygen tension ($PaO_2$) less than or equal to 55 mmHg (7.32 kPa) or a $SpO_2$ less than or equal to 88%; $PaO_2$ less than or equal to 59 mmHg (7.85 kPa), or an $SpO_2$ less than or equal to 89% if there is evidence of cor pulmonale, right heart failure, or erythrocytosis (hematocrit>55%); a reduction of $PaO_2$ to 55 mmHg or less, or of $SpO_2$ to 88% or less during exercise (which is typically indicative of the interstitial lung disease etiology of chronic obstructive pulmonary disease)[4]. Home oxygen therapy has multiple limitations, including limitations in mobility/activity of daily living, overall quality of life, access to $O_2$ delivery by patients is limited overall (particularly worldwide), and evidence in severe-moderate hypoxemia is limited and evidence is unclear on the level of benefit for LTOT in exercise-induced hypoxemia process.

Another challenge is patients are typically required to undergo a waiting period post-exacerbation before receiving the prescriptive diagnosis for home oxygen therapy[5]. Interestingly, exercise-induced symptomatic hypoxemia leads to significant worsening in the six-minute walk test and overall quality of life. In addition, up to 11% reduction in $SpO_2$ in the six-minute walk test doesn't qualify patients for supplemental oxygen leaving them with limited treatment options[6]. Clinically, this reduction in $SpO_2$ may be associated with reduced exercise capacity.

It is possible that methods and devices to improve this exercise-induced arterial hypoxemia (EIAH) that frequently effects patients with even mild chronic obstructive pulmonary disease could be well-accepted in the medical community[7].

From an epidemiologic perspective, it is estimated that ⅓ of direct medical costs are associated with oxygen therapy at a cost of more than $2.9 billion per year in the United States[8]. Despite attempts to regulate usage to populations with proven medical benefit, home oxygen use increased 33.5% from 2001 to 2010[9].

Despite the costs, guideline adoption by multiple international societies, and widespread use of oxygen therapy, the applicant is aware of only two trials (wherein patients had severe hypoxemia as defined above) conducted over thirty years ago that have shown a mortality benefit[4]. Moreover, other LTOT trials have only minimally shown exercise, quality of life, and hemodynamic benefit[4].

LTOT was defined in the British Medical Research Council landmark trial (e.g. one of the two trials that showed a mortality benefit, as described above) as supplemental $O_2$ for more than 15 hours per day[10]. However, home oxygen in the real-world is used for a longer period of time than intended by the guidelines, for all indications—including supplemental oxygen[11]. These time periods are a significant portion of a person's conscious hours. Additionally, approximately 40% of all patients receive some form of oxygen therapy[9].

Despite the widespread prescription for supplemental oxygen therapy, the equipment required to deliver the oxygen is burdensome enough to limit daily activity[12]. This is a major factor that directly impacts the overall compliance of patients leading to a vicious clinical cycle that translates to minimal long-term mortality, exercise and quality of life benefit.

In view of the above, it is apparent that there is a need for methods and devices to treat hypoxemia while improving respiratory symptoms without the high cost and patient burden associated with oxygen therapy. Additionally, there is evidence that mortality could be improved in patients suffering from severe hypoxemia. Moreover, clinical evidence exists to suggest improved oxygenation could help drive substantial improvements in exercise capacity and quality of life (and possibly, mortality).

OBJECTS AND SUMMARY OF THE INVENTION

It is an object of the present invention to provide treatments and methods that greatly reduce the patient burden that results from numerous restrictive and debilitating conditions that are manifested by the condition of hypoxemia.

These objects and many more not specifically elucidated herein are achieved by the methods and devices contemplated by the present invention whereby a patient is evaluated for baseline oxygen levels, and then an intervention is performed to improve the baseline oxygen levels and then the patient is monitored to ascertain/sustain the improved oxygen levels. Embodiments disclosed herein as well as many more embodiments that can be inferred from those disclosed herein are contemplated by the present invention.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
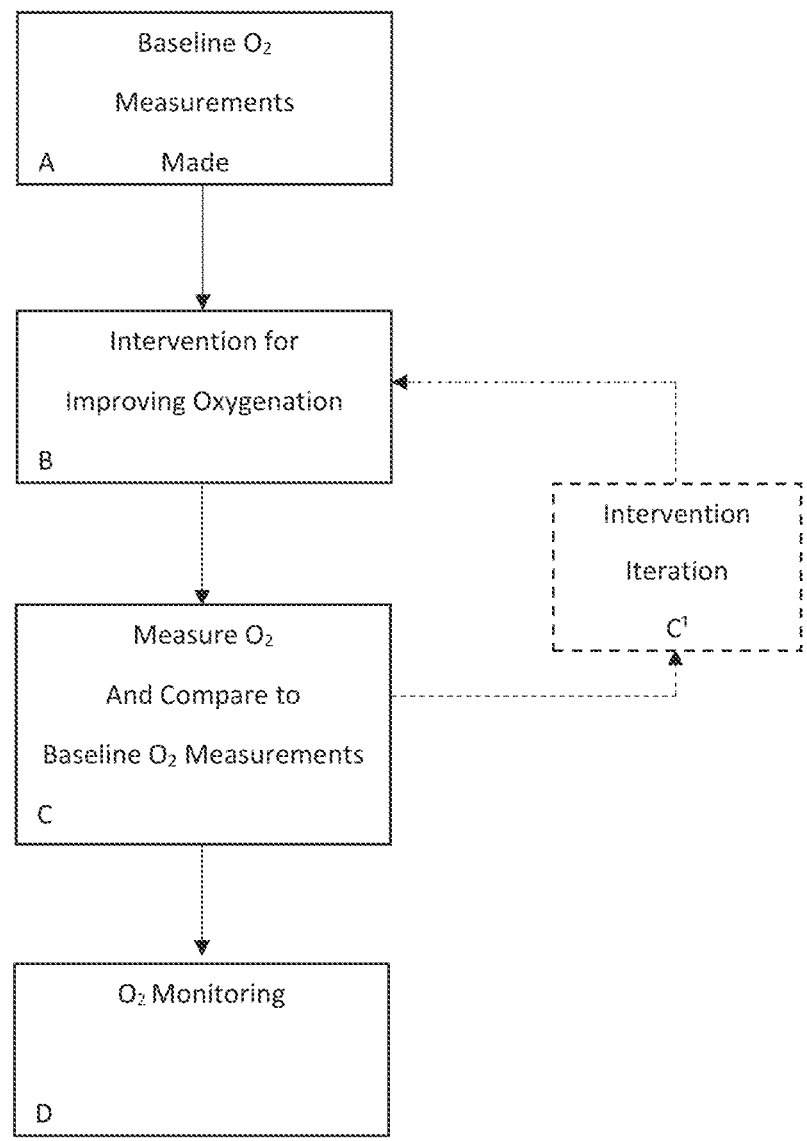
FIG. 1 depicts a protocol of treating hypoxemia in accordance with a preferred embodiment of the present invention.

Supporting background information along with specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

General Definition of Hypoxemia

As discussed above, hypoxemia is defined as an abnormally low level of oxygen in the blood (i.e., low partial oxygen tension). This is defined clinically using $PaO_2$ and/or $SpO_2$. These parameters are usually measured during rest, but in some cases, hypoxemia can be induced with exercise and definitions have evolved accordingly.

Absolute clinical values, according to current guidelines, are defined above. However, other groups define hypoxemia as a $PaO_2<80$ mm Hg or a $SpO_2<95\%$ and severe hypoxemia as a $PaO_2<60$ mm Hg or a $SpO_2<90\%$[13].

For present purposes, hypoxemia as used herein should be deemed to refer to generally accepted definitions as known to those skilled in the art, with the above examples being important benchmarks and guidelines yet also exemplary in nature.

Ventilation/Perfusion (V/Q) Matching

An important tool used to explain many etiologies of hypoxemia is V/Q matching. The general purpose of this section is to explain V/Q matching and the means by which it can be characterized. This description is useful to understanding some of the mechanisms, methods, and embodiments by which the present invention alleviates hypoxemia.

V/Q matching is the idea that perfectly matched ventilation and perfusion, in terms of regional volumetric flow, wastes neither ventilated oxygen nor blood pumped by the heart. In theory, the lung is divided into functional "units," and the unit-isolated volumetric flow of ventilated air is divided by the unit-isolated volumetric flow of perfused blood at any given time (e.g. over the duration of a ventilatory cycle). This ratio then makes up a distribution of V/Q values where, ideally, the median ratio is equal 1 with a tight distribution as shown in the graph below.

More specifically, when ventilation outpaces perfusion, the ratio is greater than 1, and ventilation is said to be wasted. When perfusion outpaces ventilation, the ratio is less than 1, and perfusion is said to be wasted. This latter scenario is termed venous admixture. An extreme case of venous admixture is the so-called physiologic shunt, where there is no ventilation for any amount of perfusion. Either of these scenarios can be attributed to various physiologic and pathophysiologic states.

In this regard, shown below is a schematic showing a scenario of low V/Q, wherein a lung unit is over-perfused relative to ventilation (left), a lung unit that is V/Q matched (middle), and a scenario of high V/Q, wherein a lung unit is over-ventilated compared to perfusion (right). Both the graph above and the schematic below are from Petersson and Glenny[14].

In general, high V/Q ratios are not associated with hypoxemia, while low V/Q ratios can be induced by various physiologic and pathophysiologic states that are associated with hypoxemia. Low V/Q can be measured to ascertain the presence of these underlying various physiologic and pathophysiologic states.

Practically, V/Q is quantified in a variety of ways. In one method radionuclide tracer quantification is done in matched perfusion and ventilation gamma camera (scintigraphy) or single photon emission computed tomography scans[14]. Dual energy CT without radionuclides may also be used[15]. A more recent approach to quantifying V/Q using fluid dynamic modeling has been proposed and is seeing good correlation to standard metrics in chronic obstructive pulmonary disease V/Q quantification[16].

Finally, the following simplified equation[17] can be used to estimate V/Q from blood gas measurements:

$$\frac{V}{Q} = 8.63 \cdot \frac{C_a O_2 - C_V O_2}{P_i O_2 - P_A O_2} \qquad (1)$$

where the following terms and assumptions are defined below:

| Term | Definition |
|---|---|
| V | Alveolar ventilation (units of L/min) |
| Q | Pulmonary blood flow (units of L/min) |
| $C_aO_2$ | Systemic arterial $O_2$ concentration (units of mL/dL) where $C_aO_2 = [Hb] \cdot 1.39 \cdot S_aO_2 + P_aO_2 \cdot 0.003$ and all input parameters are direct measurements |
| $C_TO_2$ | Pulmonary arterial $O_2$ concentration (units of mL/dL) $C_TO_2 = [Hb] \cdot 1.39 \cdot S_TO_2 + P_TO_2 \cdot 0.003$ and all input parameters are direct measurements |
| $P_iO_2$ | Pressure of inspired oxygen (units of mmHg) $P_iO_2 = F_iO_2 \cdot (P_{Atmospheric} - P_{H_2O})$ |
| $P_AO_2$ | $PO_2$, also known as oxygen tension, in the alveolar gas (units of mmHg) $P_AO_2 = F_iO_2 (P_{Atmospheric} - P_{H_2O}) - P_aCO_2/R$ and R, the respiratory quotient, is typically assumed to be equal to 0.8 |

This equation assumes that blood gas concentrations are constant with time, that the lung V/Q is spatially homogeneous, that inspired and expired gas volume are identical, that minimal $O_2$ loss occurs between the pulmonary veins and arterial blood sampling site, and that the hemoglobin disassociation curve can be used to calculate $O_2$ concentrations.

It is worth noting, however, that V/Q matching is not, in fact, spatially homogenous across the lung. The V/Q ratio generally increases from the inferior to the superior part of the lungs as depicted in the graphs below[18]. This is driven by gravity driving preferential blood flow distribution more towards the inferior region of the lung. Additionally, superior alveoli see more negative pressure and are larger than alveoli distributed toward the inferior part of the lung.

More specifically, V/Q increases toward the superior portion of the lungs. The lack of spatial homogeneity in V/Q matching is driven by gravity, anatomical differences, and unequal expansion of alveoli under negative intrathoracic pressure during inspiration. Graphs taken from Levitsky[19].

It is possible that pathologic states that limit ventilatory dynamics through fluid transudate compressing on the alveoli, such as pulmonary edema, could lead to increased incidence of venous admixture. Moreover, methods and devices in accordance with the present invention that preferentially divert blood flow to the superior portion of the lung could improve hypoxemia. These methods and devices are discussed in further detail below.

Generic Etiologies of Hypoxemia

Hypoxemia occurs when oxygen uptake by hemoglobin in red blood cells is reduced. This can be attributed to five main causes[20]. These causes are:

1. Hypoventilation

Hypoventilation is defined as a state where reduced ventilated air enters the alveoli either through reduced respiration rate, bronchial restriction, or reduced tidal volume, among other causes. This decreases the oxygen tension in the alveoli ($PAO_2$).

However, the alveolar-arterial oxygen pressure gradient ($PA-aO_2$) does not change because the arterial oxygen tension ($PaO_2$) decreases proportionally with the decrease in $PAO_2$. Patients with this condition respond to supplemental oxygen (increased $FiO_2$) because supplemental oxygen increases $PAO_2$ and $PaO_2$ correspondingly increases. In terms of V/Q matching, hypoventilation is a scenario of low V/Q driven by reduced ventilation in the presence of sustained flow. Hypercapnia is present in hypoventilation-type hypoxemia[17].

2. Diffusion Limitation

Gases exchange between alveolar gas and pulmonary capillary blood by passive diffusion. In a basic sense, diffusion limitation is the idea that there is some phenomenon that doesn't allow for an adequate amount of time or provide an adequate $O_2$ concentration gradient for maximal oxygen diffusive uptake by hemoglobin across the alveolar capillary membrane. This scenario can derive from a variety of physiologic and pathophysiologic scenarios, including exercise, interstitial lung disease, and possibly pulmonary arterial hypertension[21,22].

In normal physiology, exercise results in increased cardiac output which reduces the time red blood cells are exposed to oxygen diffusion at the alveolar capillaries. This reduces oxygen uptake via diffusion despite normal ventilation (and consequently $PAO_2$). This type of diffusion limitation, due to increased cardiac output (i.e. flow) and reduced transit time, has been experimentally demonstrated in athletes[23]. In exercising athletic individuals, mean transit time (MTT) decreased from 1.05 seconds to 0.46 seconds during exercise at rates of 0-90% maximum oxygen consumption ($VO_{2Max}$). This decrease in MTT was correlated with increased cardiac output and capillary blood volume, as well as decreased $PaO_2$[24].

In this regard, the graphs below depict the relationship between exercise intensity (VO2Max), cardiac output (Q), mean red blood cell transit time (MTT), pulmonary capillary blood volume (VC), and partial pressure (also called oxygen tension) of arterial oxygen (PaO2). Exercise requires an increase in cardiac output. This increase in cardiac output was associated with decreased MTT and PaO2. The reduction in PaO2 with decreased MTT forms the basis for diffusion-limited hypoxemia at high cardiac outputs. Graphs taken from Warren et al.[24].

As mentioned, reduced MTT limits oxygen uptake via diffusion at the alveolar capillary level as demonstrated by reduced $PaO_2$, despite maintained $PAO_2$. Thus, another indicator of diffusion limitation is an increase in the alveolar-arterial oxygen pressure gradient ($PA-aO_2$) driven primarily by the reduction in $PaO_2$ via diffusion limitation.

Another study has shown that even a modest increase of approximately 10 mmHg in mean pulmonary artery pressure (without corresponding increases in mean arterial pressure) is correlated with decreased MTT[25]. So, despite normal or slightly reduced cardiac outputs in pulmonary hypertension[26], it is possible that pressure-derived decreases in MTT contribute to diffusion-limited hypoxemia. This suggests that an etiology of hypoxemia in pulmonary hypertension may be diffusion limitation.

An additional condition associated with diffusion limitation as the etiology of hypoxemia is interstitial lung disease[20]. In this condition, the alveolar interstitial membrane, across which oxygen diffuses, is thickened. The thickening is not evenly distributed throughout the lung. At rest, this may be compensated for by the compensatory mechanism of hypoxic vasoconstriction. However, several studies have demonstrated marked hypoxemia at exercise[27] (i.e.

increased cardiac output/flow). It is also possible that high pulmonary pressures contribute to diffusion limitation across this thickened membrane as flow re-distribution via hypoxic vasoconstriction is no longer enough to compensate for reduced MTT. It is possible to have normal V/Q with interstitial lung disease.

Additional diseases associated with some degree of diffusion limitation are emphysema-type chronic obstructive pulmonary disease (COPD) with blood capillary preservation, severe pneumococcal pneumonia (which carries a 30% in-hospital mortality[28]) and pulmonary edema[29].

Diffusion limitation, driven by reduced MTT, may be an underlying physical reason for hypoxemia in other etiologies presented here—including physiologic shunting.

Hypercapnia is not often found in diffusion-limited hypoxemia[17].

3. Decreased Pressure of Inspired Oxygenation $(PiO_2)$[20]

Reduced $PiO_2$ is more straightforward than diffusion limitation. An example of decreasing pressure of inspired oxygen can be demonstrated by looking at the impact of altitude on $PaO_2$. Decreasing barometric pressure at high altitudes drives a decrease in the pressure of oxygen in the alveoli, despite a constant fraction of inspired oxygen. This etiology of hypoxemia is mechanically similar to hypoventilation, except for a V/Q ratio that is close to normal in this scenario. The alveolar-arterial oxygen pressure gradient ($PA$-$aO_2$) does not change because the $PaO_2$ decreases proportionally with the decrease in $PAO_2$. People in this scenario respond to supplemental oxygen ($FIO_2$) because supplemental oxygen increases $PAO_2$, and $PaO_2$ correspondingly increases.

4. Physiologic Shunt

True physiologic right-to-left shunts exist anatomically via the bronchial/pleural[30] and thebesian[31] circulation. However, venous admixture can create a physiologic shunt in extreme cases where no blood is oxygenated as it traverses the alveolar capillary. It seems, in practice, that lung units where 100% shunting exist are rare, and shunting may generally be thought of as a case of increased relative perfusion.

The graphs below show scenarios of low V/Q attributed to venous admixture. The first graph shows a scenario of venous admixture where there is some degree of ventilation. The second graph shows a scenario of true physiologic shunting where there is evidence of blood flow with no ventilation. This situation is rare and happens most commonly in interstitial lung disease with exercise or in scenarios of atelectasis such as acute respiratory distress.

As mentioned before, the underlying physical cause of physiologic shunting or venous admixture may be attributed to reduced MTT.

5. Abnormal Ventilation to Perfusion Ratio (V/Q)

Generic low ventilation to perfusion ratios are simply either a result of low ventilation, high flow, or combinations thereof. It can happen in the following disease states: COPD (emphysema or bronchitis), which limits ventilation relative to preserved blood flow. Pulmonary hypertension, of most types, which may be associated with decreases in MTT. Asthma, where bronchial constriction limits ventilation relative to preserved blood flow. Acute respiratory distress syndrome induced by pneumonia or sepsis, which generally leads to loss of ventilation in large lung regions, causing physiologic shunt flows in excess of 50%.

Approaches to Treating Hypoxemia

The following approaches to treating hypoxemia are exemplary for the methods and devices in accordance with the present invention. Individual approaches or combinations thereof are all viable as a basis for treating hypoxemia in accordance with the present invention.

1. Pressure Reduction in Pulmonary Circulation

The pulmonary system can be thought of as a lumped resistance-capacitance-inertance circuit analogue. Pressure, in this scenario, is the potential or "voltage" that drives flow through this circuit.

If pressure [$\Delta P$] is reduced in the pulmonary artery, flow [Q] would have to decrease by the $Q=\Delta P/R$ relationship law, assuming constant resistance [R] in the pulmonary circuit during the acute time frame. The decrease in global volumetric flow and associated reduction in flow velocities would increase the time for hemoglobin molecules to transit the alveolar capillary mass (i.e. the MTT). This increase in time maximizes oxygen uptake and increases arterial saturation. This increase in arterial saturation would increase the amount of mixed venous saturation, assuming constant uptake by the downstream organ systems, at least in the acute time frame. Lastly, the now higher oxygen content in the pulmonary circulation could mitigate further hypoxic vasoconstriction.

This would create a positive feedback cycle that would provide the potential to substantially increase the chronic probability of rarely becoming hypoxemic, thereby avoiding the critical maladies of the hypoxemic state.

2. Reducing the Triggering Pressure Signal

Elevated pulmonary artery pressures are associated with an increase in the amount of venous admixture due to inappropriate vasoconstriction and intimal thickening. Since the vasoconstriction is thought to be a neurologic response due to high pulmonary pressures exciting the pulmonary artery stretch receptors, change and likely reduction in the triggering pressure signal that causes vasoconstriction will lower the vascular tone (i.e. resistance) of the pulmonary circulation.

Acute canine studies have shown that simple balloon dilation can induce an increase in pulmonary artery pressures and pulmonary vascular resistance[32]. In a simplistic view, balloon dilation is like the stretch that a patient with pulmonary hypertension pathophysiology may experience. Research has demonstrated that the stretch induced by high pressure is associated with increased sympathetic nervous system activity[33]. It is likely that this, along with and/or separate from hypoxic vasoconstriction, reduces vessel diameter and increases pulmonary artery pressure and pulmonary vascular resistance.

In a similar scenario, reducing mean pulmonary artery pressure, while maintaining CO, will result in reduced blood flow velocity and increased MTT. First, by reducing PA pressure there is potential for improved right ventricular function—specifically, right ventricular stroke volume is maintained at a lower working pressure (i.e. reduced right ventricular afterload). The assumption is that in the setting of increased pulmonary artery pressures, the right ventricle is working against a higher than normal afterload. Due to limited cardiac reserve of the right ventricle, the increase in afterload does not result in increased cardiac output. It is possible that reducing afterload can be done without the consequence of reduced cardiac output.

Secondly, a reduced pulmonary artery pressure may disrupt the sympathetic innervation of the pulmonary arterioles, reversing vasoconstriction of the vessels, resulting in relaxation and vasodilation. In the context of maintained cardiac output and vessel dilation, the blood flow velocity will be reduced since the volumetric flow rate (i.e. cardiac output) is equal to the blood flow velocity times the cross-sectional area of the pulmonary arterioles. The consequence of reduced blood flow velocity is that the red blood cells spend more time in the capillaries, i.e. an increase in MTT.

It is possible that a chronic pathophysiological remodeling of the vessel wall intimal layer occurs due to increase pressure and wall tension in the pulmonary arteries and arterioles. This remodeling process results in an increase in smooth muscle cells which are vasoreactive, and response to signaling pathways that can result in vasoconstriction (reduced vessel lumen diameter) and vasodilation (increased vessel lumen diameter).

The sympathetic nervous system can become overly active in the setting of chronic pulmonary hypertension, resulting in vessel constriction. The exact signaling mechanisms can vary, but may include stretch and wall shear stress induced sympathetic activation, i.e. an increase in blood pressure and wall shear stress in the pulmonary arteries may give rise to increased sympathetic activation which further leads to vessel constriction and chronically elevated blood pressure (a positive feedback loop).

In summary, a decrease in resistance would open vessels and slow mean transit time, thereby increasing oxygen content. This increased oxygen in the arterial system would enrich the mixed venous oxygenation, assuming constant oxygen consumption by the target organ systems. This increase in mixed venous oxygenation would translate to the pulmonary circulation and lead to less hypoxic vasoconstriction. This would be a wholly positive loop that would improve the status of hypoxemic of patients.

For the above mechanism a potential solution is a R-R shunt with a critical design consideration of its size— specifically, the amount of shunted flow will need to be compensated by the RV in order to maintain cardiac output, while at the same time result in a large enough reduction in PA pressure to reduce RV afterload and disrupt the sympathetic vasoconstriction.

3. Flow Restriction

Reducing the over-perfusion of non-ventilated alveoli increases oxygenation. This reduction can be achieved by flow restriction/minimization within the pulmonary circulatory system. For example, by improving V/Q via flow restriction, the sensation of dyspnea in heart failure with preserved ejection fraction upon exercise and/or hypoxemia induced by sleep apnea could be minimized. Both alleviatory affects could minimize further ischemia and interstitial damage, increasing mortality.

A key mechanistic insight is that in many cases of over-perfusion, and in pulmonary hypertension in particular, perfusion of poorly ventilated areas of the lung preferentially increases[34]. This increase in perfusion to poorly ventilated regions causes an increase in venous admixture with an associated reduction in global V/Q, and most importantly, an increase in arterial hypoxemia. It is therefore desired to increase V/Q and improve hypoxemia by identifying either over-perfused and/or under-ventilated regions and by subsequently reducing flow to these regions.

It is noted that practical tools[16] exist for low-cost identification of such regions, and that the methods and embodiments described herein can be practically applied to increase arterial oxygen saturation.

As flow is more evenly redistributed to well-ventilated regions and oxygenation initially improves, the mechanical pressure gradient between the alveoli and capillaries can further decrease. During progressive cardiac cycles, more returned mixed venous oxygen could further release the hypoxic vasoconstriction response in the alveoli. Ultimately, this could lead to less progressive ischemia. Additionally, it should be noted that pressure reduction from right-to-right shunting could be considered a form of flow limitation as the reduced trans-pulmonary gradient can no longer force the same amount of flow through the pulmonary vessel tree of identical resistance to that of the resistance pre-shunt.

Limiting the flow in the main trunks of the PA, for example, may minimize the amount of over-perfusion that can occur, in case examples of exercise in normal physiology, pulmonary hypertension, or bronchial restrictions/ COPD. A targeted reduction in flow to areas of low ventilation or relative over-perfusion could also be done locally. These methods are described more in the respective embodiments in accordance with the present invention.

Lastly, a potential application of blood flow restriction/ reduction could be chronic thromboembolic pulmonary hypertension (CTEPH). In CTEPH, thromboembolic material (e.g. from a dislodged deep vein thrombosis) causes one or more occlusions in the pulmonary circulation. This, combined with the assumption of maintained cardiac output, causes pulmonary pressures to increase. This is primarily caused through increases in local resistance in occluded pulmonary branches that drive blood flow redistribution to other alveolar regions. This decreases MTT and presumably leads to higher rates of venous admixture and low V/Q ratios. It is thus plausible that either global blood flow restriction or restriction of flow in over-perfused regions could increase V/Q ratios, thereby alleviate hypoxemia[35].

Monitoring the Efficacy of the Approaches

The following tests may be useful in monitoring the efficacy of the aforementioned approaches and also assist in identifying additional components of those approaches or even in identifying new approaches: cardiopulmonary exercise testing, regional blood flow resistance, V/Q scans, computed tomography, magnetic resonance imaging, echocardiography, blood gases, and peripheral oxygenation and tests that generate mean transit time. A new technical tool known as functional respiratory imaging could also be performed to assess the efficacy of the approaches.

Devices and Methods

General Protocol

As will become clear from the discussion below, there are numerous ways to implement the above-described approaches to treat hypoxemia. Each of these ways constitute preferred embodiments of the present invention. It will be appreciated, however, that the disclosed preferred embodiments are by no means exhaustive to the ways, combinations of ways and nuanced ways in which the present invention can be practiced. There is, however, a general protocol that to be followed in implementing the disclosed embodiments.

Referring to FIG. 1, a first step A is to make baseline measurements of the patient that is experiencing hypoxemia. These measurements include, but are not limited to, hemodynamics (pressures, flows, heart rate, etc.), shunt volumetric flows, blood oxygenation percentages ($SvO_2$, $SpO_2$, $SaO_2$, pulmonary $O_2$ saturation, etc.), Ventilation/perfusion dynamics (dynamic V/Q ratio, A-a gradient), Neurohormone levels (ANP, BNP, etc.), blood chemistry (hemoglobin concentration, RBC concentration, etc.), and Ventilatory Parameters ($VO_2max$, $VE/VCO_2$), FEV1, FEV1/FVC ratio.

Next, an intervention B is performed using any of the devices and methods in accordance with the preferred embodiments disclosed herein.

Either during or immediately after the intervention, the baseline measurement is repeated C and compared to the original baseline measurements A in order to evaluate the efficacy of the intervention. That comparison may lead in one embodiment where the intervention is titrated or modified C' and repeated until the intervention has been optimized. In one preferred embodiment, the measurements can also be made at baseline, intra-procedurally and post-procedurally both at rest and with exercise conditions. For example, cardiopulmonary exercise testing (CPET) can be performed pre and post procedure.

Lastly, patient is monitored D, as needed, following the completion of the intervention.

Interventions

Shunting

A. Shunt Location

In one preferred embodiment, the intervention is constituted by creating a shunt within the right side of the circulatory system, that is, the creation of a shunt from one vessel on the right side of the heart to a second vessel which is also on the right side of the heart. The right side of the heart refers to any part of the circulatory system that contains desaturated blood. For the purposes of the present invention, this will be referred to as "right-to-right" shunting. Such shunting primarily uses the pressure reduction approach to treating hypoxemia but may introduce mechanistic aspects of flow reduction. Such shunting can be created with either implantable shunts or non-implantable shunting techniques, or combinations thereof.

Figure 2:
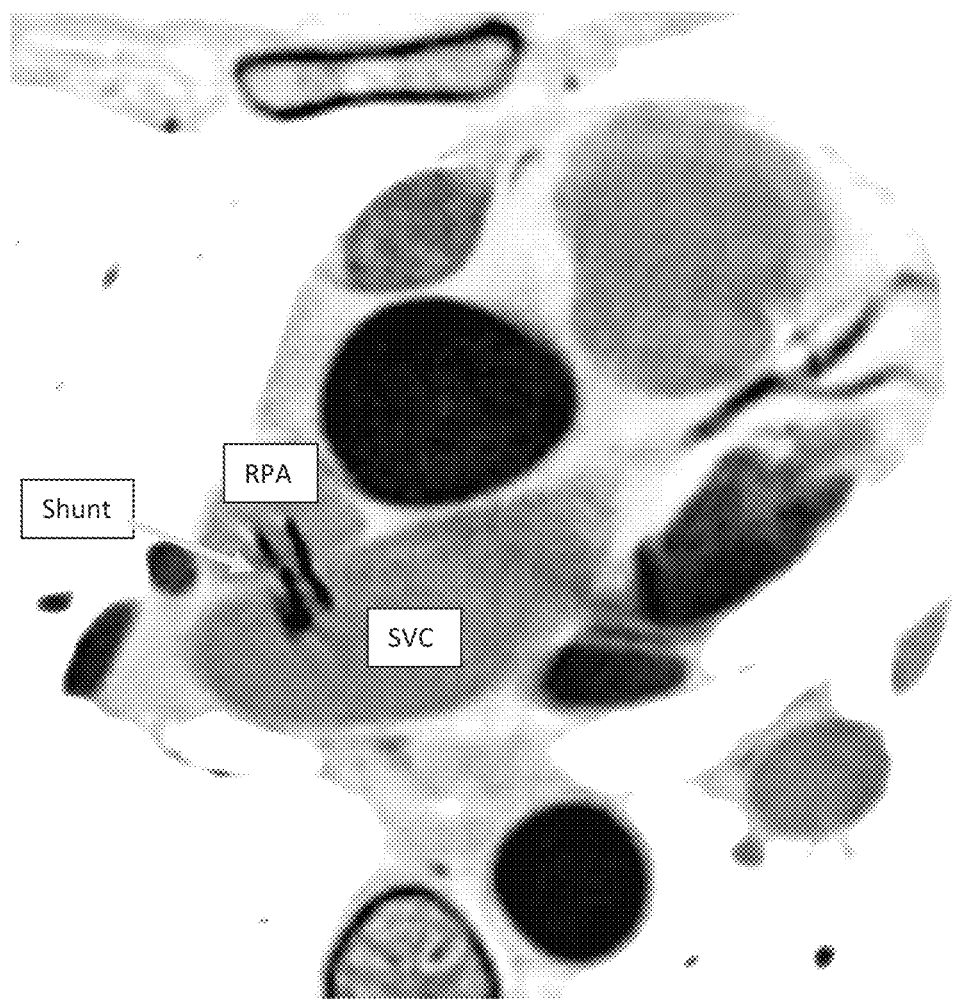
FIG. 2 depicts an embodiment of intervention for treating hypoxemia in accordance with a preferred embodiment of the present invention.
Figure 3:
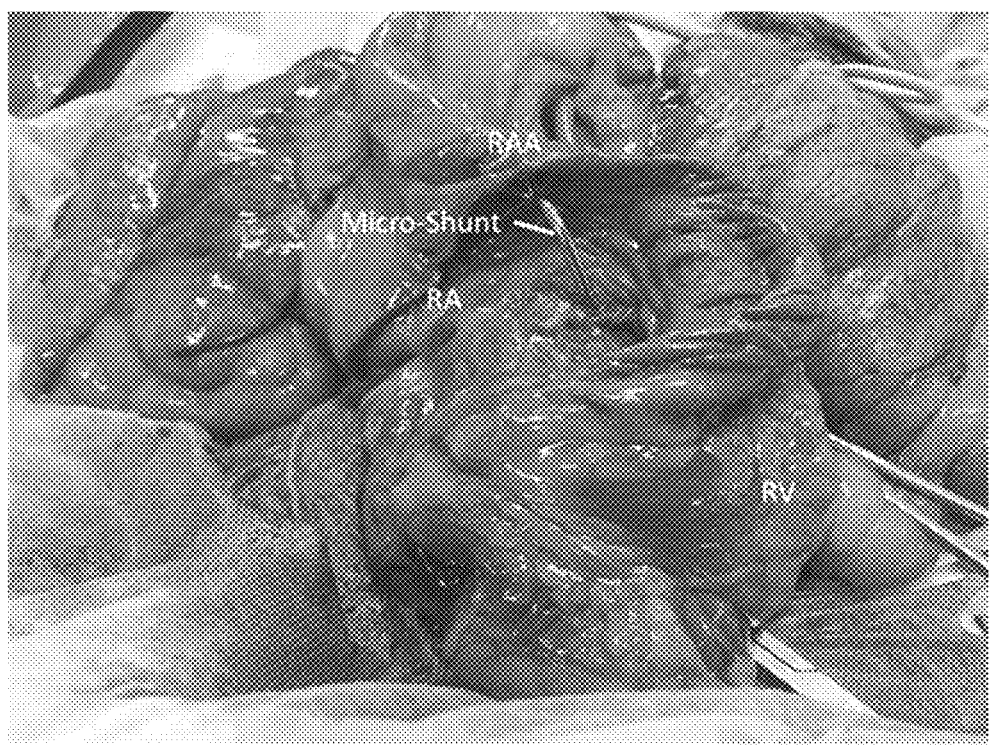
FIG. 3 depicts an embodiment of intervention for treating hypoxemia in accordance with a preferred embodiment of the present invention.
Figure 4A:
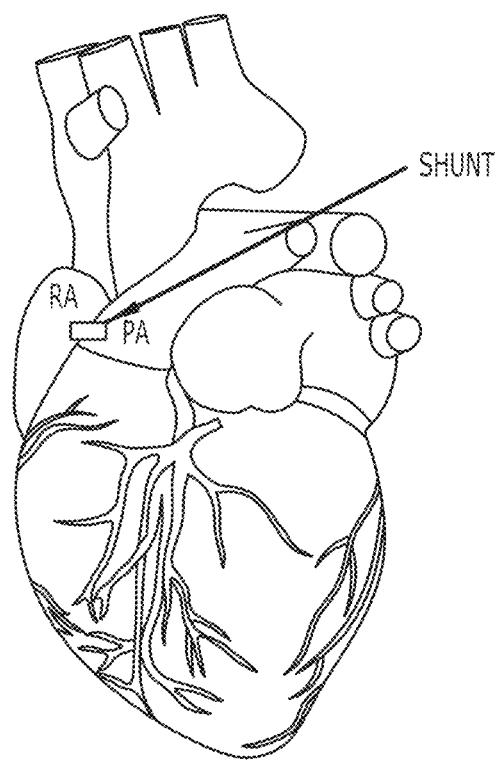
FIGS. 4A-4B depicts an embodiment of intervention for treating hypoxemia in accordance with a preferred embodiment of the present invention.

In preferred embodiments, this right-to-right shunt is created between the right pulmonary artery and the superior vena cava is depicted in FIG. 2. In other preferred embodiments, the right-to-right shunt is made from the main pulmonary artery to right atrial appendage as shown in FIG. 4A, the right ventricle to inferior vena cava, or a small conduit that creates a trivial amount of tricuspid regurgitation to limit forward flow, as depicted in FIG. 3. Examples of right-to-right shunts are found in U.S. patent application Ser. No. 16/576,704 filed Sep. 19, 2019 entitled Methods and Technology For Creating Connections and Shunts Between Vessels and Chambers of Biologic Structures, (hereinafter the "'704 Application") the entirety of which is hereby incorporated by reference.

Essentially all right-to-right shunts are contemplated by the present invention. In other words, any venous to venous chamber or vessel that would allow for a pressure gradient that would activate the physiology described above to increase oxygenation levels is contemplated by the present invention. Additional exemplary locations include, but are not limited to, the azygous vein to inferior vena cava (IVC), the right ventricle to the IVC, any subbranch of the pulmonary artery to the IVC or the right atrium.

Figure 4B:
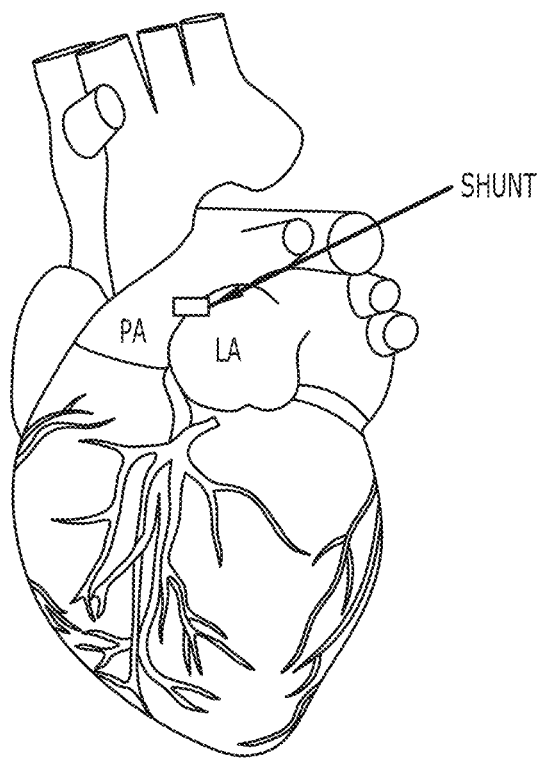

Notwithstanding the foregoing, small right-to-left shunts are also within the purview the present invention. In one preferred embodiment, a small right-to-left shunt between the main pulmonary artery and left atrial appendage as shown in FIG. 4B could provide the pressure-reducing affect to treat hypoxemia with minimal desaturation and flow rates that maintain global cardiac output. Another potential minimal right-to-left shunt could be created between a pulmonary arterial branch and one or more of the pulmonary veins.

B. Implantable Shunt

Figure 5:
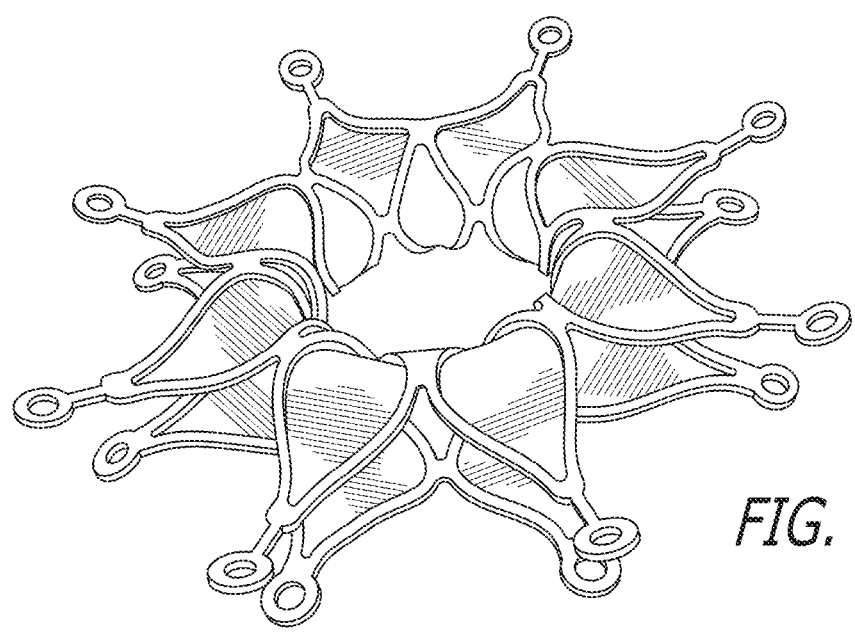
FIG. 5 depicts an embodiment of intervention for treating hypoxemia in accordance with a preferred embodiment of the present invention.

Numerous implantable shunts are contemplated in the present invention, including each of the shunt devices disclosed in the '704 Application, and which are specifically included by reference in the present application. One representative shunt 400 from the '704 application is depicted in FIG. 5 herein and, in a preferred embodiment, is used to shunt between the RPA and the IVC.

Figure 6:
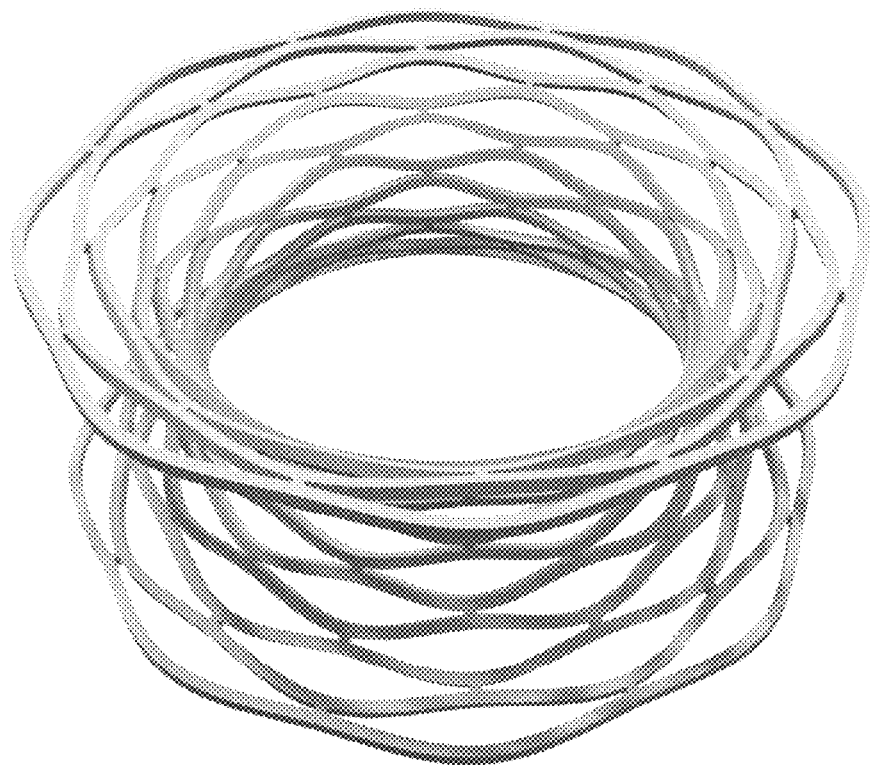
FIG. 6 depicts an embodiment of intervention for treating hypoxemia in accordance with a preferred embodiment of the present invention.
Figure 7:
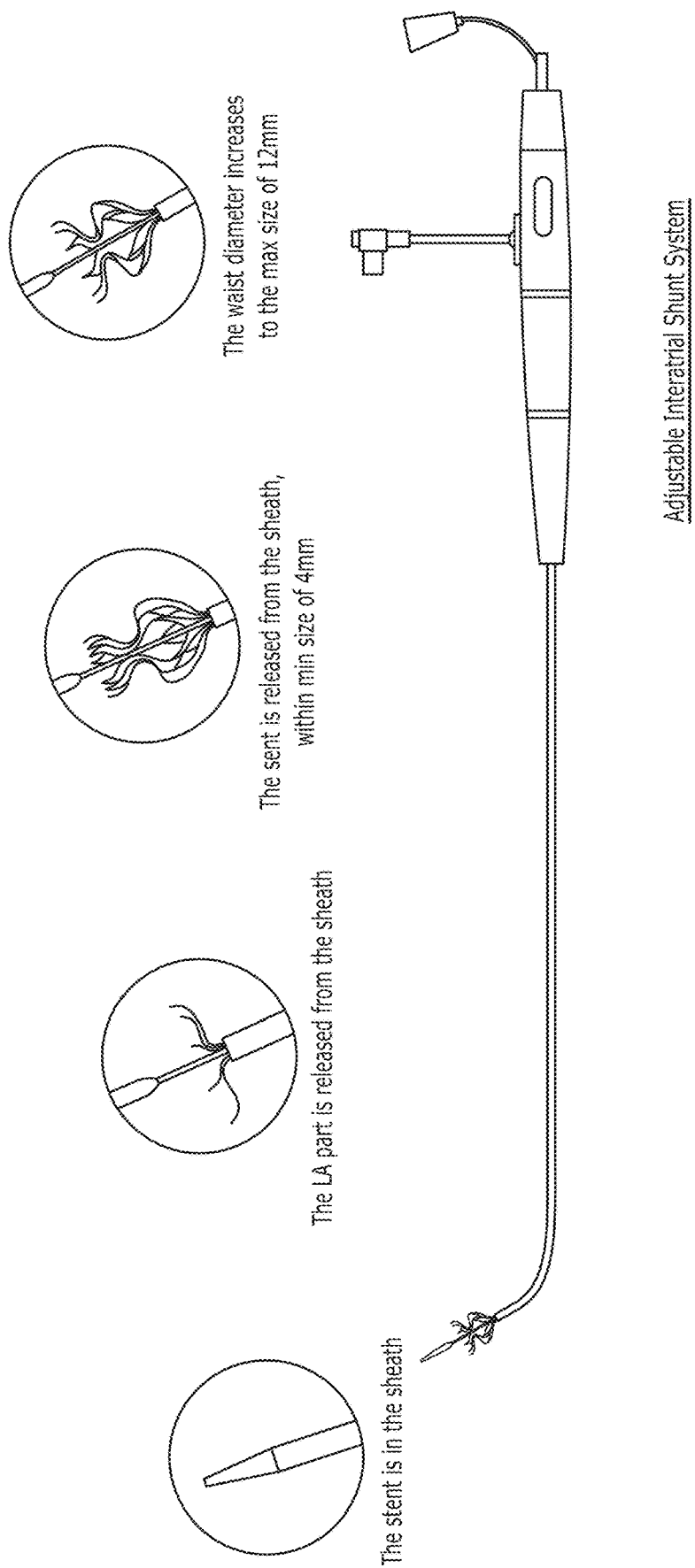
FIG. 7 depicts an embodiment of intervention for treating hypoxemia in accordance with a preferred embodiment of the present invention.

Implantable shunts disclosed in U.S. application Ser. No. 62/896,144 filed Sep. 5, 2019 entitled Rivet Stent and U.S. Provisional Application Ser. No. 62/942,631 filed Dec. 2, 2019 entitled Rivet Stent (the "'144 and '631 Applications") are also contemplated in the present invention, both of which are also incorporated by reference into the present application. One representative shunt 500, known as a rivet stent, from the to '144 and '631 Applications is depicted in FIG. 6 and, in a preferred embodiment, is used to shunt between the RPA and the SVC.

All designs and methods previously disclosed in the '704 Application and the '144 and '631 Applications can be utilized to increase vascular compliance (discussed below) or create a partial shunt or communication channel between two vessels or chambers that are part of the venous cardiovascular system for the purpose of treating hypoxemia.

Other implantable shunt designs can also be utilized, such as those disclosed in U.S. Pat. No. 8,172,896 (Corvia), U.S. Pat. No. 9,706,997 (Rox), U.S. Pat. No. 8,070,708 (V-Wave), U.S. Pat. No. 9,789,294 (Edwards) and U.S. Publication No. 2007/0225760 (Occlutech), each of which is hereby incorporated by reference.

C. Non-Implantable Shunt

Non-implantable shunting for the treatment of hypoxemia in accordance with the present invention can be achieved using shunt procedures such as the adjustable shunt size creation through ablation as disclosed with the NoYa™ system depicted in FIG. 6.

Figure 8:
FIG. 8 depicts an embodiment of intervention for treating hypoxemia in accordance with a preferred embodiment of the present invention.

Another non-implantable approach to shunting is to cut an aperture between vessels, e.g., mechanical coring, as disclosed in WO 2019/109013 (Alleviant Medical), which is herein incorporated by reference. An exemplary depiction of such coring is set forth in FIG. 8.

Each of these approaches can be used to create a shunt for treating hypoxemia without leaving behind a permanent implant and are encompassed by the present invention.

Denervation

Another embodiment of the present invention for intervention to treat hypoxemia is pulmonary artery denervation (PADN).

It is known that PADN can decrease pulmonary artery pressures and since pulmonary artery denervation causes a reduction in pressure, PADN can cause an increase in blood oxygenation in accordance with at least the approach of reducing the pressure triggering signal as discussed above.

Methods and technologies available to perform PADN include, but are not limited to, radiofrequency ablation (RF), cryoablation, laser ablation, pulsed electrical field ablation, radiation, drug block, alcohol ablation.

Figure 9:
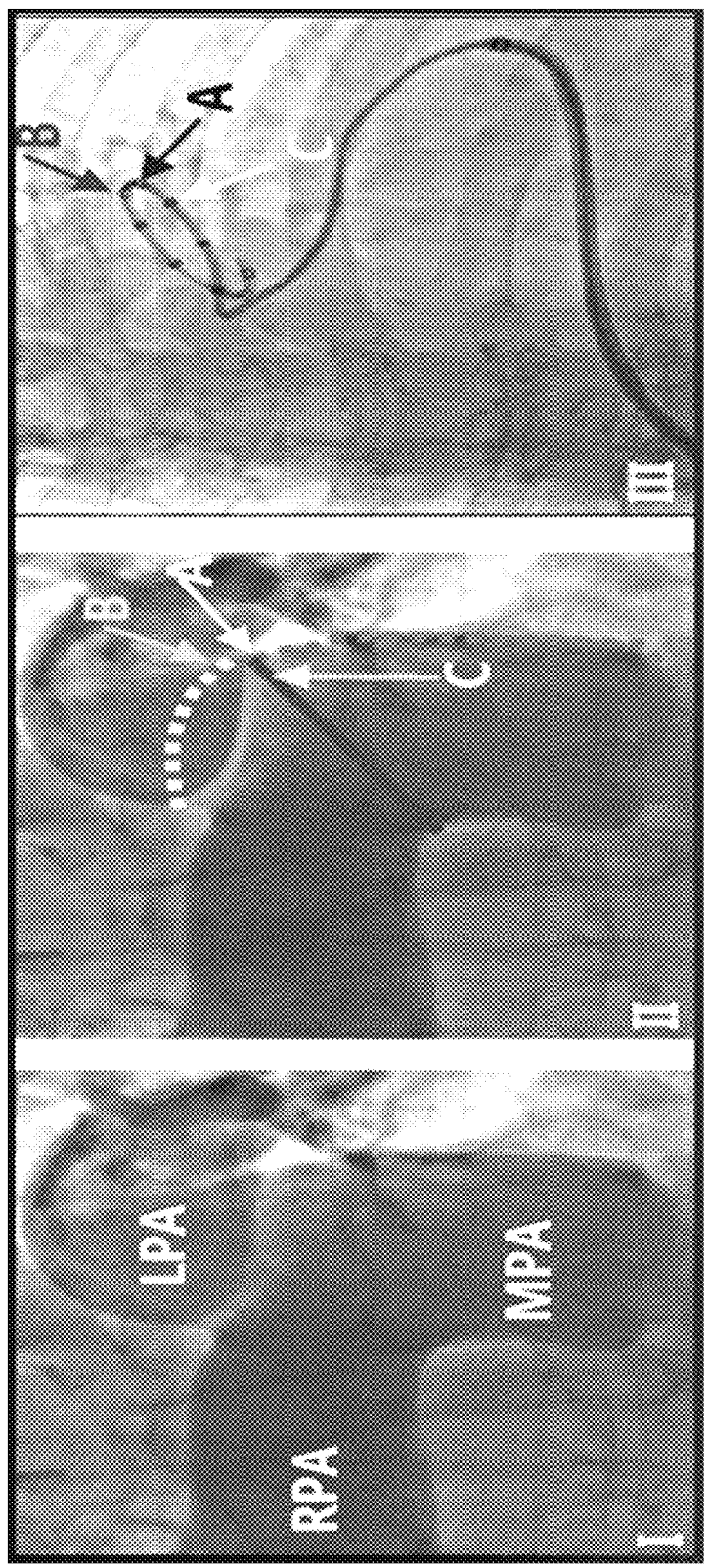
FIG. 9 depicts an embodiment of intervention for treating hypoxemia in accordance with a preferred embodiment of the present invention.

One example of such a PADN intervention is depicted in the X-Rays of an actual PADN as set forth in FIG. 9. U.S. Publication No. 2018/0140347 (Pulnovo Medical) also depicts method and devices for performing PADN that can be used to treat hypoxemia in accordance with the present invention and is hereby incorporated by reference.

Restrictions

Another embodiment for intervention in treating hypoxemia in accordance with the present invention is to include restrictors into the pulmonary circulatory system consistent with at least the restrictor approach discussed above.

Figure 10:
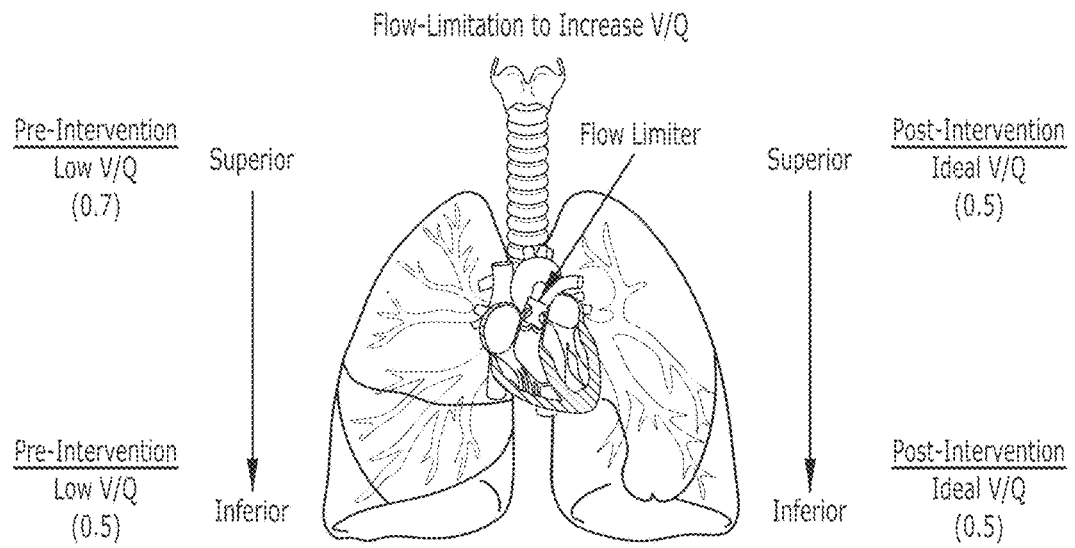
FIG. 10 depicts an embodiment of intervention for treating hypoxemia in accordance with a preferred embodiment of the present invention.

In this regard, a device (e.g. a flow limiter, or as used interchangeably herein, a flow reducer) may be placed to provide reduction of the relative over-perfusion of non-ventilated alveoli. This could be done, for example by a flow restriction element in the main pulmonary artery (PA) as depicted in FIG. 10. Such a flow restriction element could also be placed in the right or left PA or somewhere down the vascular tree.

With further reference to FIG. 10, flow limiters may be used in the main pulmonary arterial vessels to broadly limit over-perfusion to over-perfused regions. This may be particularly beneficial in in improving exercise tolerance. By improving V/Q via flow restriction, the sensation of dyspnea in heart failure with preserved ejection fraction[36] upon exercise and/or hypoxemia induce by sleep apnea could be minimized. Both of these alleviatory affects could minimize further ischemia and interstitial damage, increasing mortality.

Flow limiters in the main trunks of the PA could minimize the amount of over-perfusion that can occur, in case examples of exercise in normal physiology, pulmonary hypertension, or bronchial restrictions/COPD.

In other embodiments, flow limiters in specific locations could aid in recruitment of healthier lung. For example, a catheter with an occlusive balloon of known diameter could be repeatably placed in a vessel of known diameter. With stepped flow rates of saline injectate, one could perceivably measure the true luminal resistance (or isolated resistance of the targeted circulatory branch, more likely). Flow could be diverted away from trees with known high resistance.

In another embodiment, computer visual aids (e.g. image juxtaposition or supposition—i.e. side-by-side panels or the fashionable "fusion" fluoroscopy/echocardiography style of imaging) could be used to view xenon-contrasted gamma scans concurrently with live contrast angiography. This could be used to place restrictors/or in still another embodiment, flow limiter(s) at regions of low V and high Q as shown in FIG. 11 where flow limitation and/or occlusion is performed to distribute blood flow away from non-functional ventilatory lung units.

As flow is more evenly redistributed, the mechanical pressure gradient between the alveoli and capillaries can further decrease. During progressive cardiac cycles, more returned mixed venous oxygen could further release the hypoxic vasoconstriction response in the alveoli. Ultimately, this could lead to less progressive ischemia. Additionally, it should be noted that pressure reduction from pulmonary shunting could be considered a form of flow limitation as the reduced trans-pulmonary gradient can the same amount of flow through a vessel tree of identical resistance to that of the resistance pre-shunt.

Figure 11:
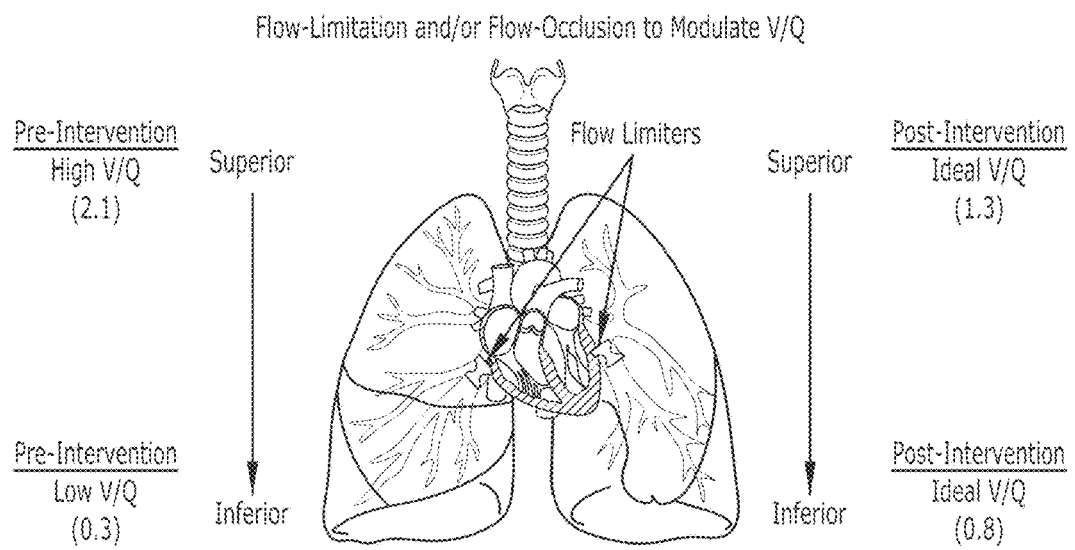
FIG. 11 depicts an embodiment of intervention for treating hypoxemia in accordance with a preferred embodiment of the present invention.

Restrictors or flow limiters in accordance with the present invention can be a stent like structure made from, but not limited to, a lasercut tube, braided structure, or implantable polymer scaffolding that has a geometry or covering that reduces the cross-sectional area of the lumen to decrease flow rate and thereby increase transit time in the pulmonary vasculature allowing for more oxygen exchange (FIGS. 10-11). This device can be placed in main pulmonary trunk, branch of the pulmonary artery, pulmonary vein, IVC, SVC, aorta or other peripheral vasculature.

Figure 12A:
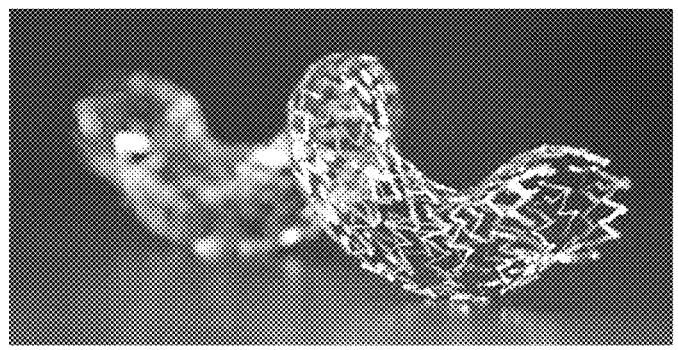
FIGS. 12A-12C depict an embodiment of intervention for treating hypoxemia in accordance with a preferred embodiment of the present invention.
Figures 12B, 12C:
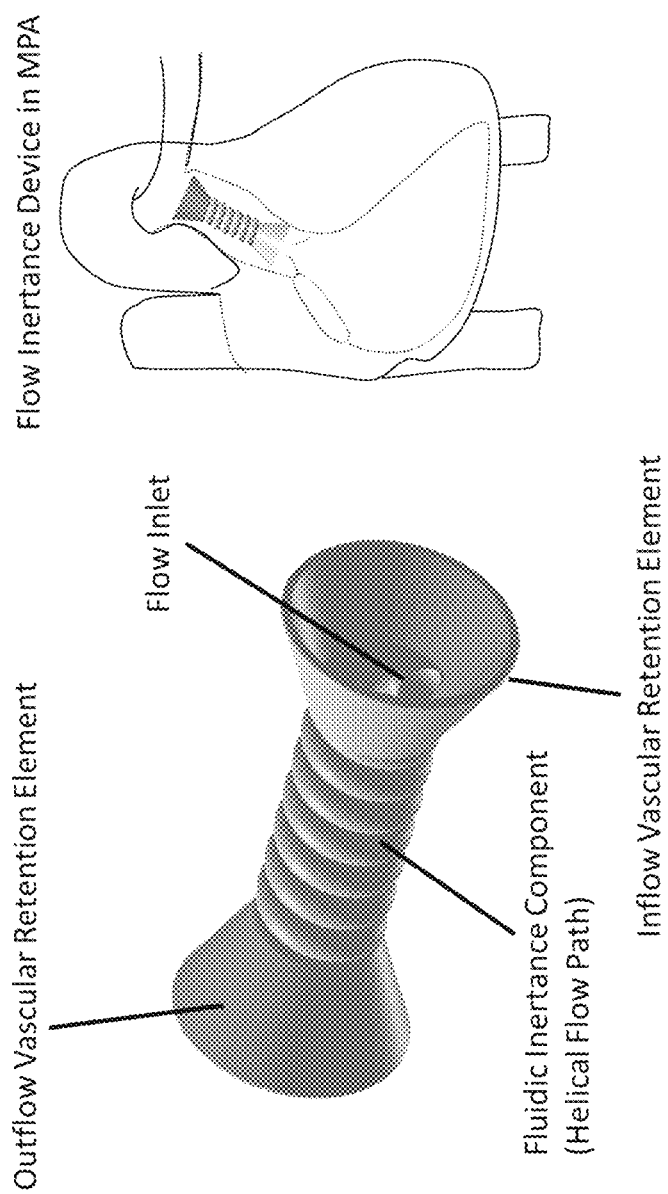

In another embodiment a device is placed in the venous/pulmonary system that creates a longer path for blood to flow through (For example, a helical stent in the IVC/SVC/PA as shown in FIGS. 12A-12C. This would slow blood flow and increase transit time. This would impact the inertance component of the pressure reduction approach discussed above. Of importance, the impact of this inertance element would become increasingly dominant at high rates of pressure ramp-up in the pulmonary artery as the right ventricle contracts (which is associated with high pulmonary artery pressure and therefore pulmonary hypertension[37]). This means that this helical path acts as a variable shunt that could reduce flow preferentially at high pressures and therefore adapt to conditions such as exercise more readily. Transit time would be increased by slowing blood flow via the increased inertance of the helical path introduced by this implant.

Figure 13:
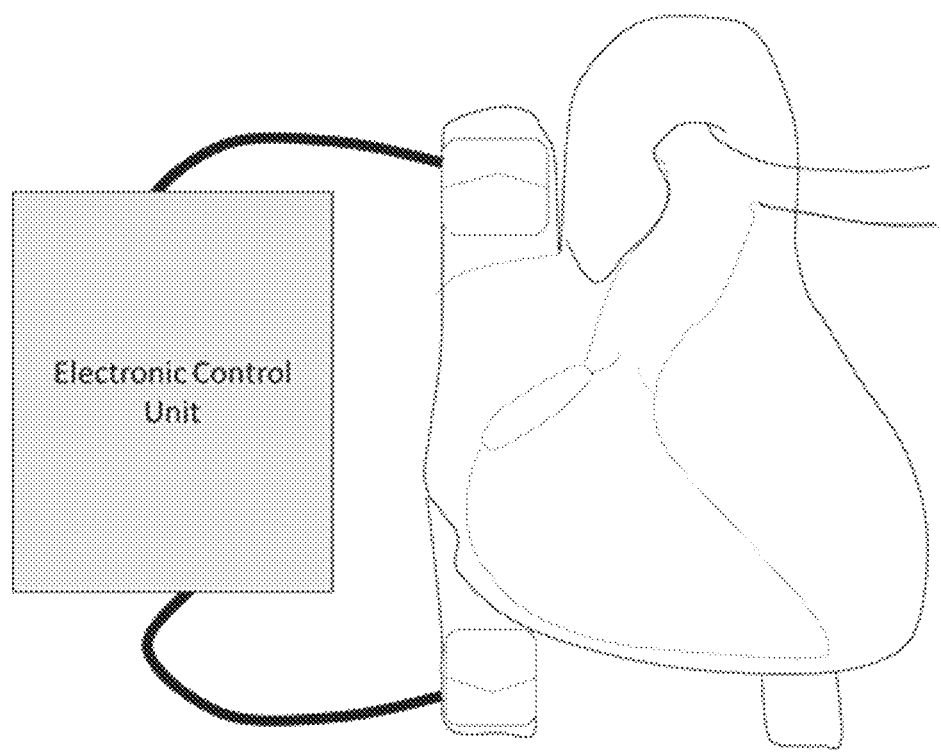
FIG. 13 depicts an embodiment of intervention for treating hypoxemia in accordance with a preferred embodiment of the present invention.

In another embodiment for the restriction intervention is to add alternating right and left pulmonary artery branch occlusion elements. This would allow for 2X transit time on each side of the lung (albeit with 2× volume). Also, alternating inferior vena cava and superior vena cava occlusion could reduce the preload on right ventricle as rendered in FIG. 13. This embodiment, for example, could be an implantable valve system that is timed to switch to physiologic parameters, including but not limited to IVC pressure, SVC pressure, RA pressure, RV pressure, PA pressure, cardiac output, etc. This reduction in preload would cause the heart to generate less afterload, per the Starling Law. This reduction in afterload would be associated with decreased pulmonary pressures and increased transit time.

Compliance

In another embodiment for intervention to treat hypoxemia, the pulmonary pulse pressure can be reduced to thereby decrease the mean transit time of red blood cells and increase diffusive $O_2$ uptake in accordance with pressure reduction approach described above, by increasing the compliance in the pulmonary circulation.

This is addressing hypoxemia from a transient perspective, which relevant considering the heart is a natively transient system. It is well-known that decreased compliance in the pulmonary circulation is linked to high pressures and proliferative interstitial fibrosis that progresses to pulmonary arterial hypertension[38].

In one embodiment, a gas-filled balloon is placed in the pulmonary circulation to provide a more compressible gas in place of non-compressible blood. This would increase the compliance in the pulmonary circulation.

Figure 14:
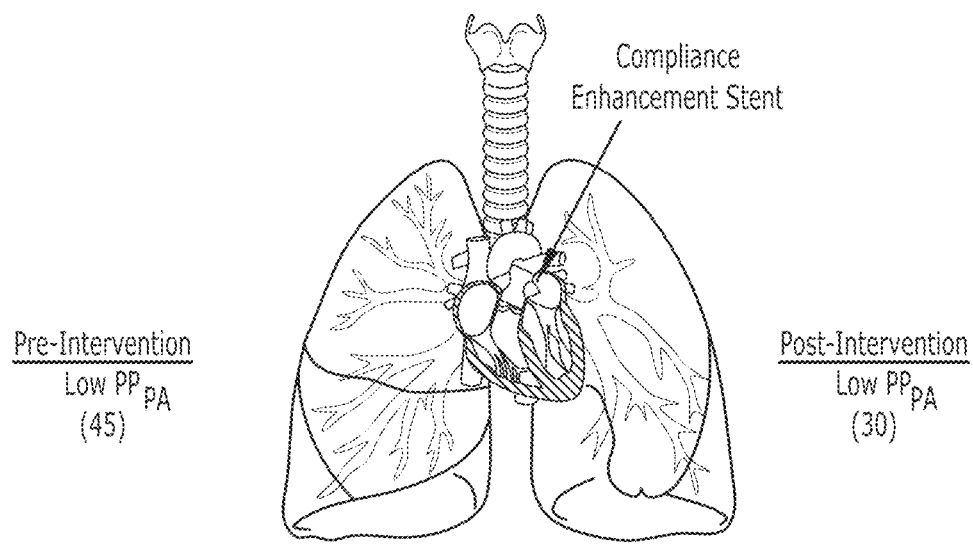
FIG. 14 depicts an embodiment of intervention for treating hypoxemia in accordance with a preferred embodiment of the present invention.

In another embodiment, a stent with implantable bladders that compress external to the original true lumen diameter could be used. With reference to FIG. 14, a covered stent graft is placed between dissected pulmonary arteries. This dissection in the PA would be controlled via creating a mechanical dissection tool or by using catheter-based laser cutting systems.

Once this external communication is created, a second graft with either compliant balloons or sheets that communicate with the space created outside the vasculature would be inserted to improve compliance in this section (FIG. 14). Shape change to increase compliance (i.e. a squarely deformed lumen, via a stent, to a circle) could also be used to increase MTT.

With further reference to FIG. 14, compliance is restored to the pulmonary circulation to reduce pulse pressure thereby addressing the problem of reduced transit time leading to less diffusive oxygen uptake. FIG. 14 shows an embodiment of compliance restoration where an externally communicating elastic membrane is placed in lieu of the rigid vasculature to improve compliance. Compliance restoration improves transit time of red blood cells by addressing the transient nature of this transmission. This attempts to restore the normal dynamics of red blood cell transit, which further increases oxygen uptake and alleviates hypoxemia.

Figure 15:
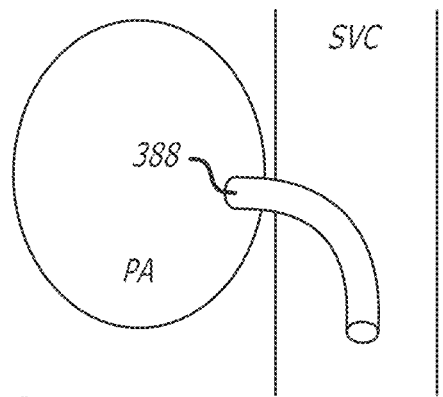
FIG. 15 depicts an embodiment of intervention for treating hypoxemia in accordance with a preferred embodiment of the present invention.

Other embodiments of introducing compliance as described above are depicted in the '704 Application, which is incorporated by reference. Examples of devices and methods that can be used to treat hypoxemia in accordance with the present invention from the '704 Application are presented here as FIGS. 15-17, wherein FIG. 15 depicts a shunt with a compliant element 388 disposed in the SVC.

Figure 16:
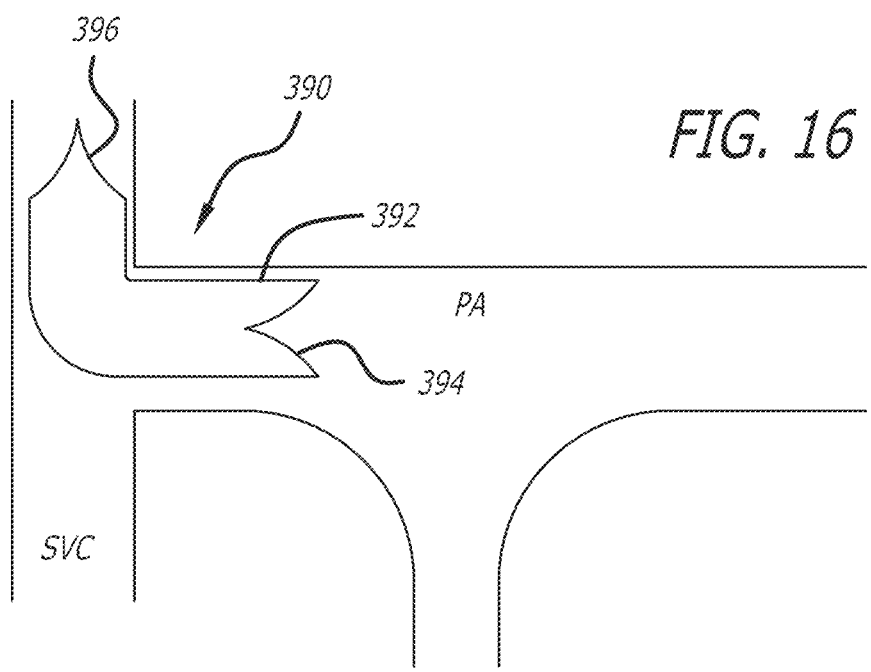
FIG. 16 depicts an embodiment of intervention for treating hypoxemia in accordance with a preferred embodiment of the present invention.
Figure 17:
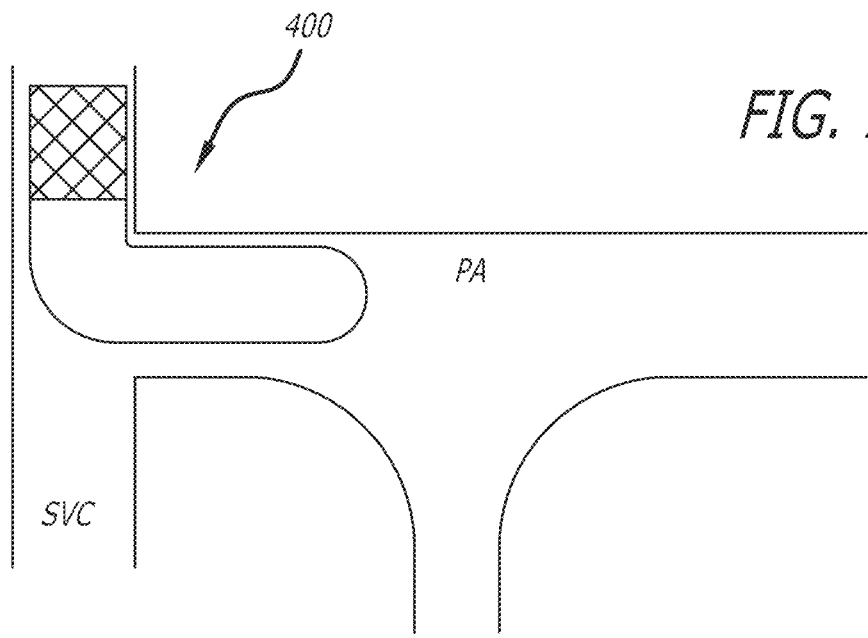
FIG. 17 depicts an embodiment of intervention for treating hypoxemia in accordance with a preferred embodiment of the present invention.

FIG. 16, shows a bi-valve shunt (valves 396, 394) with the compliant element 390 in the SVC. And FIG. 17 shows a dual compliance element 400 across the PA to the SVC.

Figure 18:
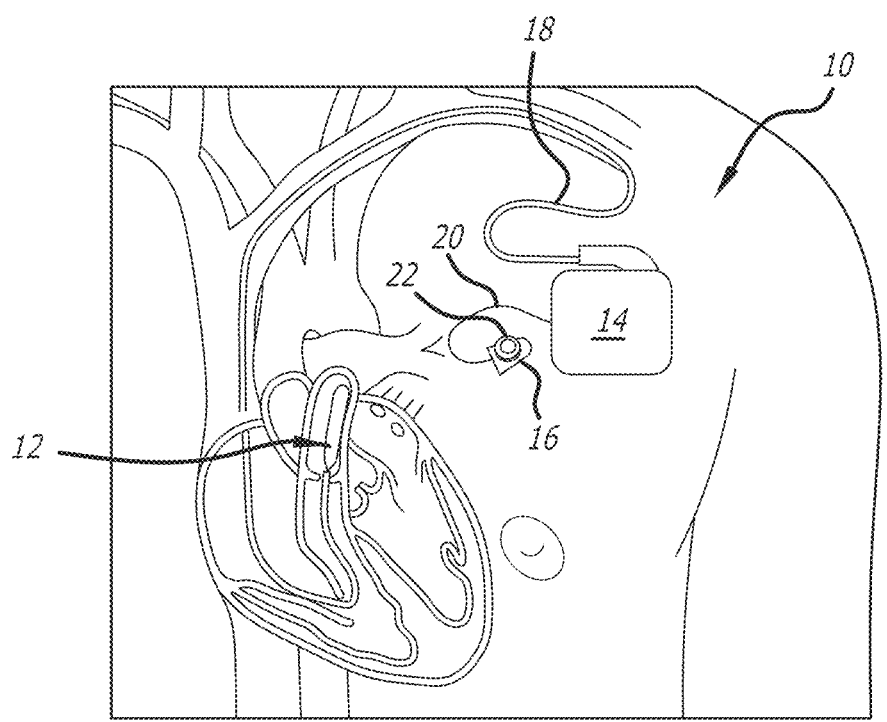
FIG. 18 depicts an embodiment of intervention for treating hypoxemia in accordance with a preferred embodiment of the present invention.
Figure 19A:
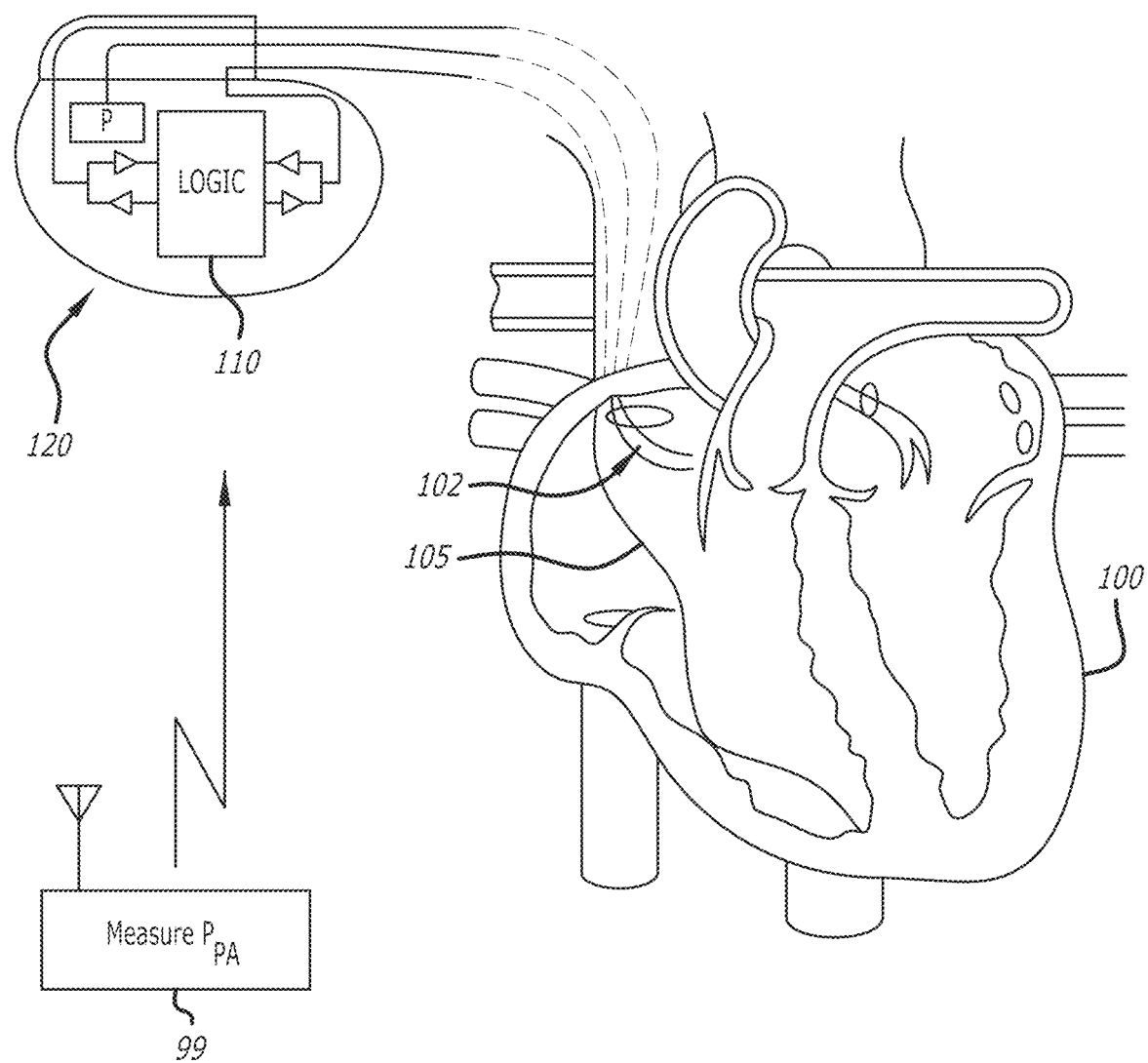
FIGS. 19A-19D depict an embodiment of intervention for treating hypoxemia in accordance with a preferred embodiment of the present invention.
Figure 19B:
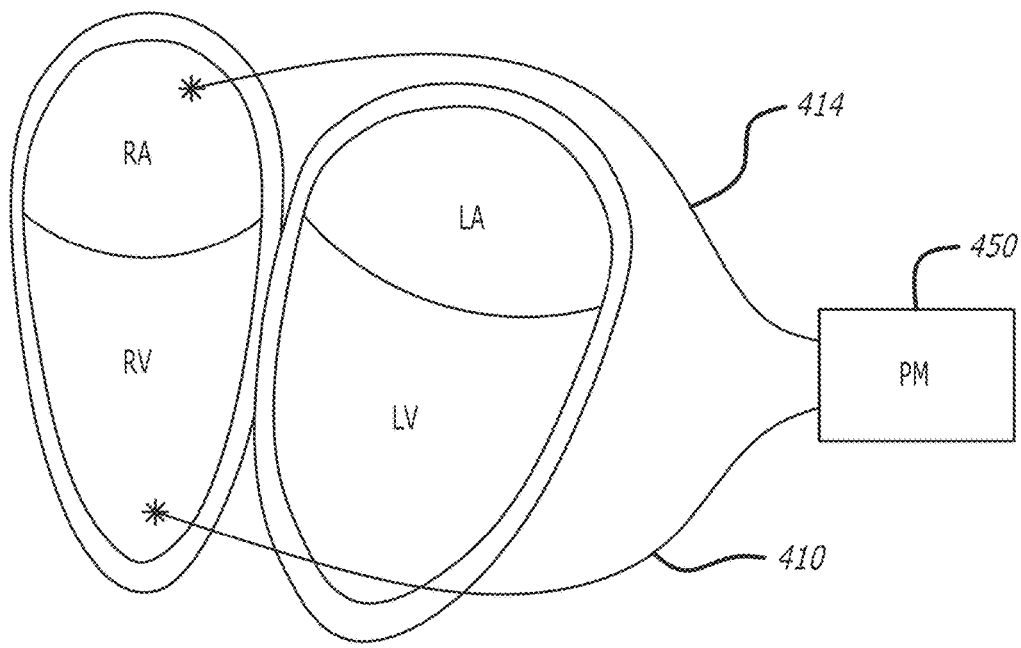
Figure 19B:
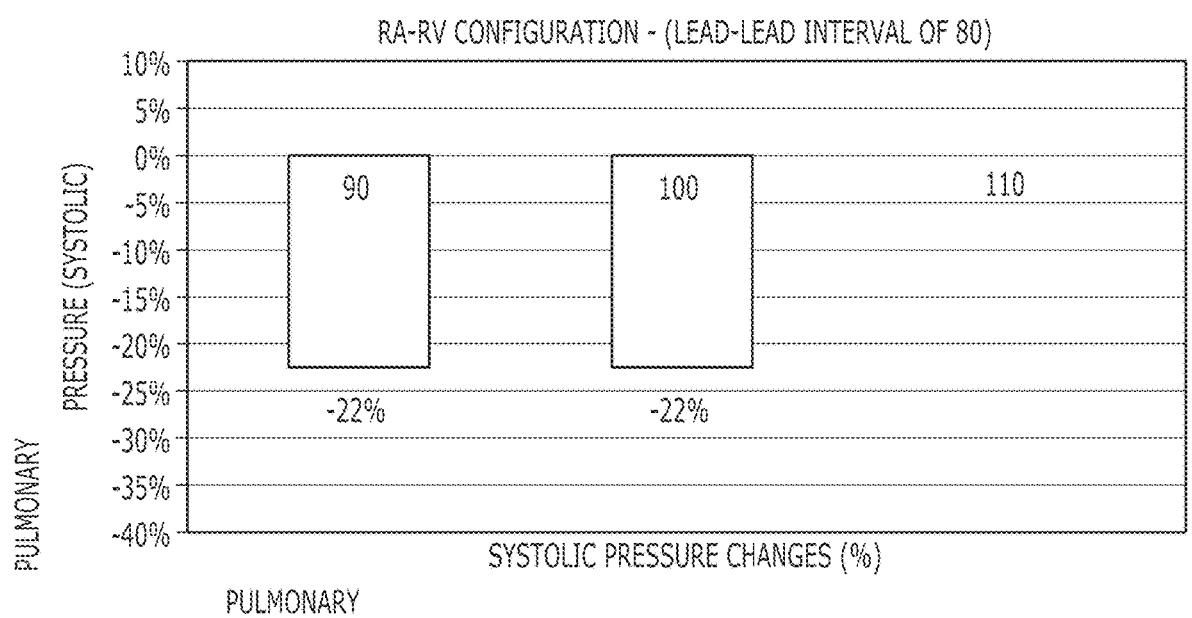
Figure 19C:
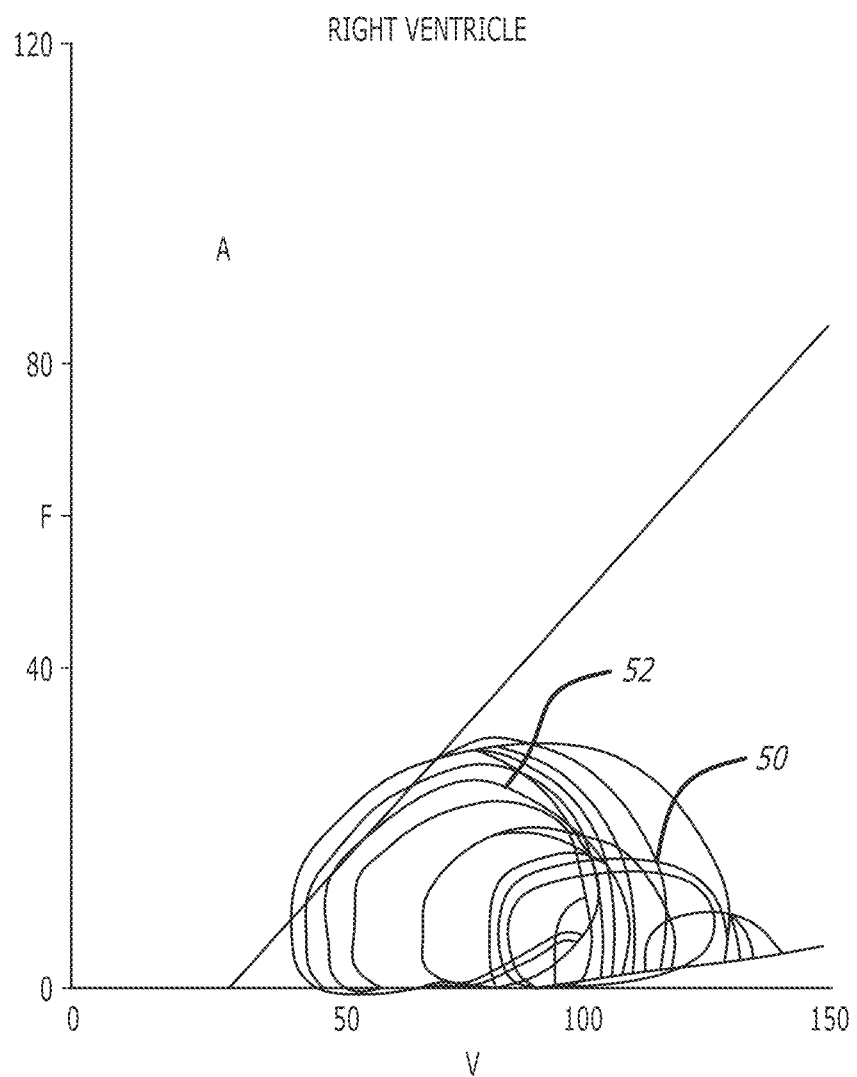
Figure 19D:
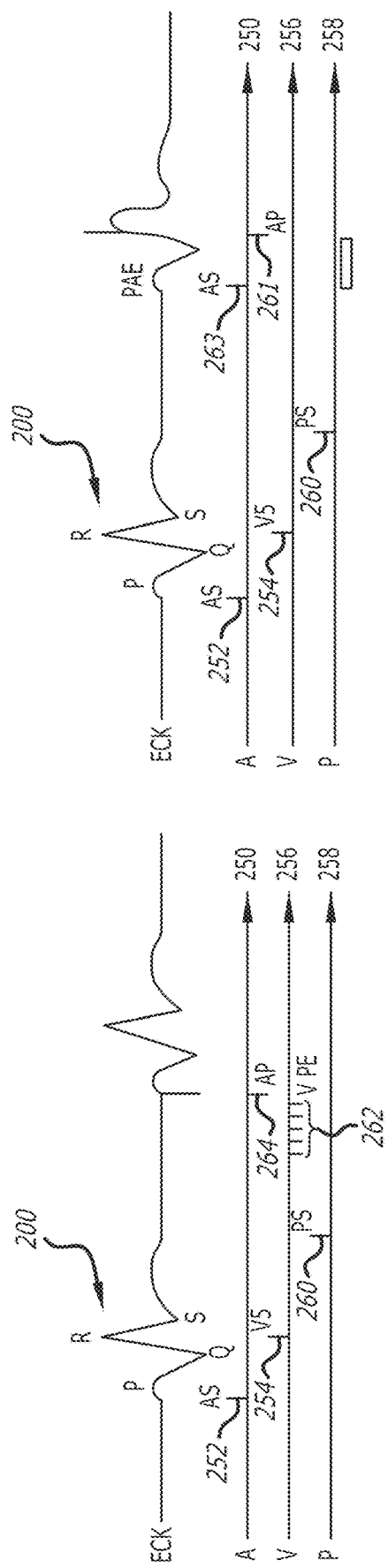
Figure 20:
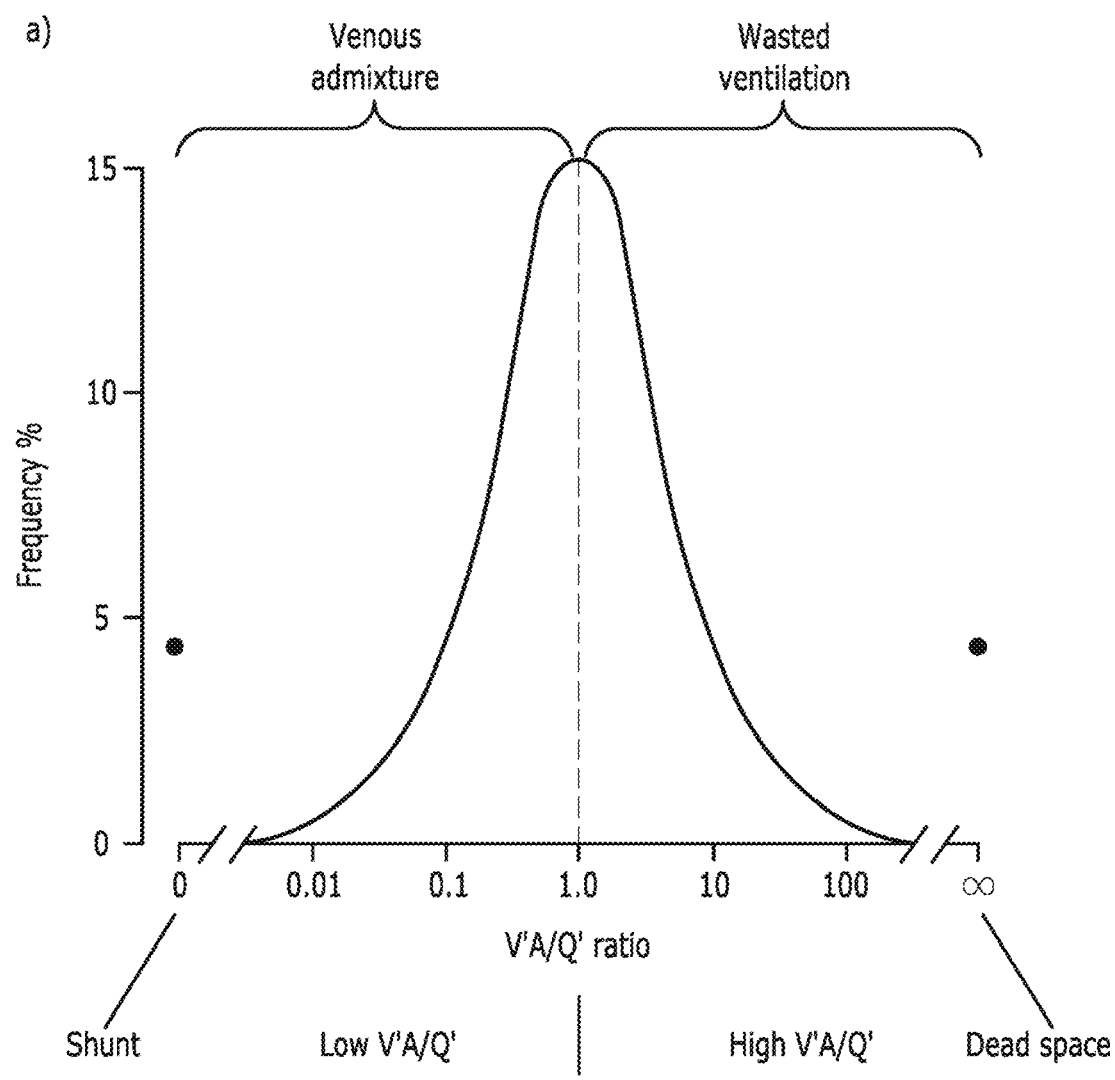
Figure 21:
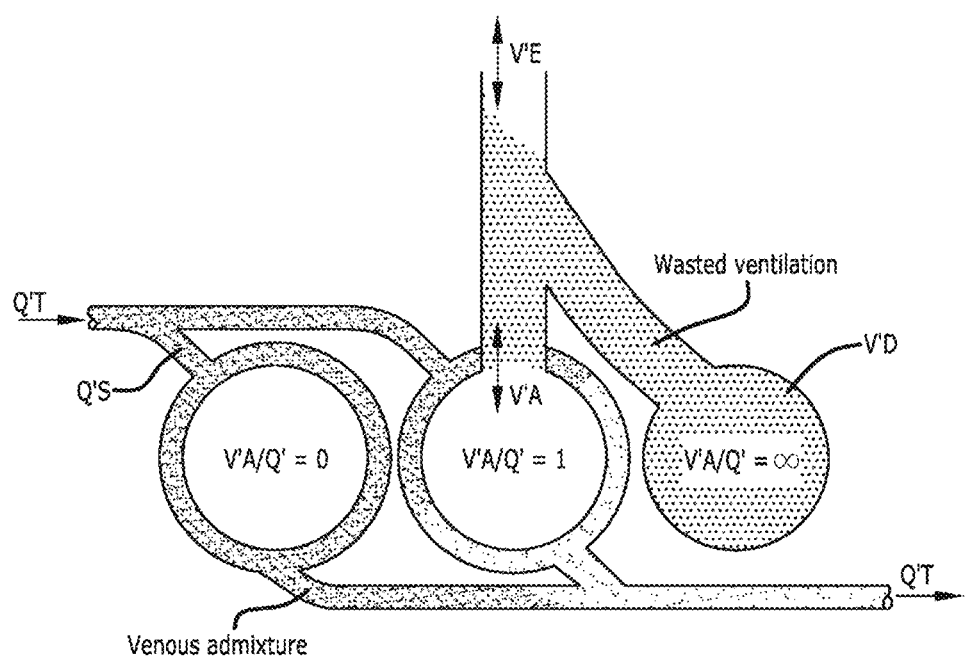
Figure 22A:
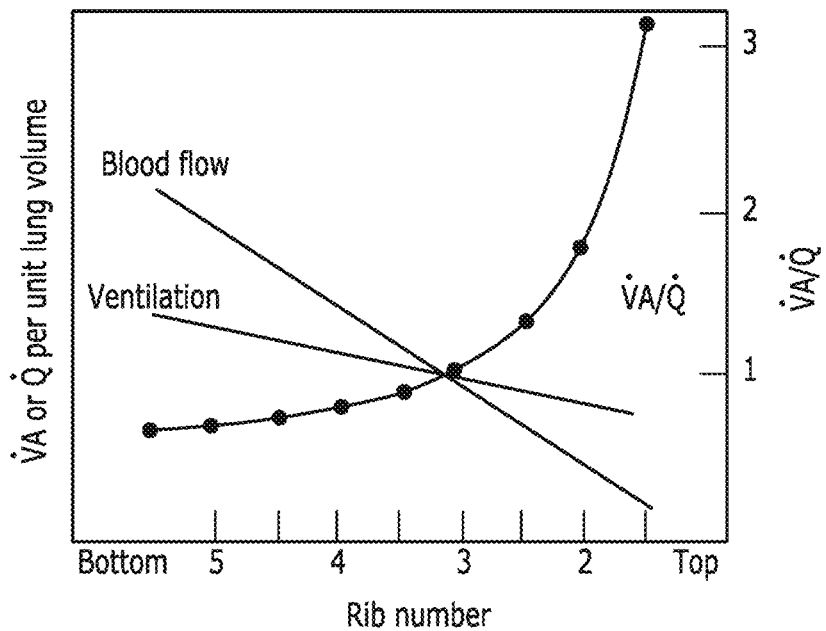
Figure 22B:
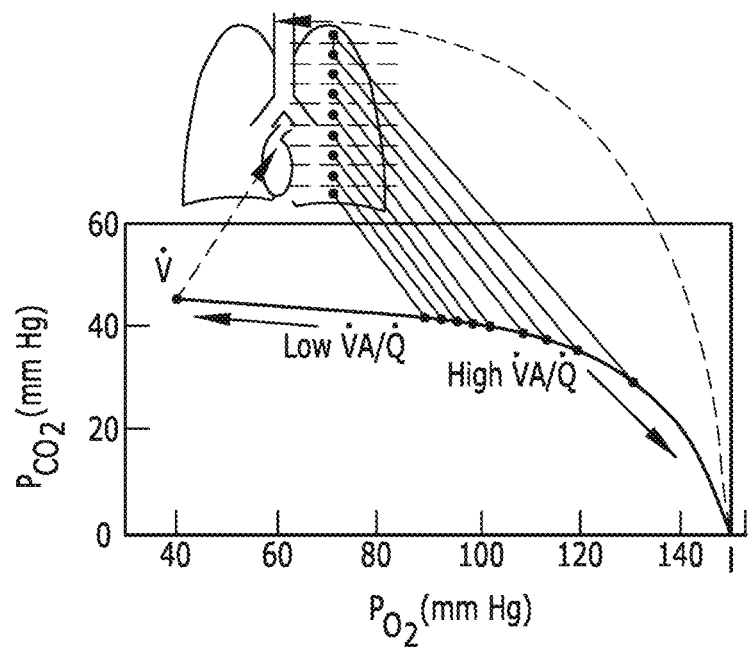
Figure 23A:
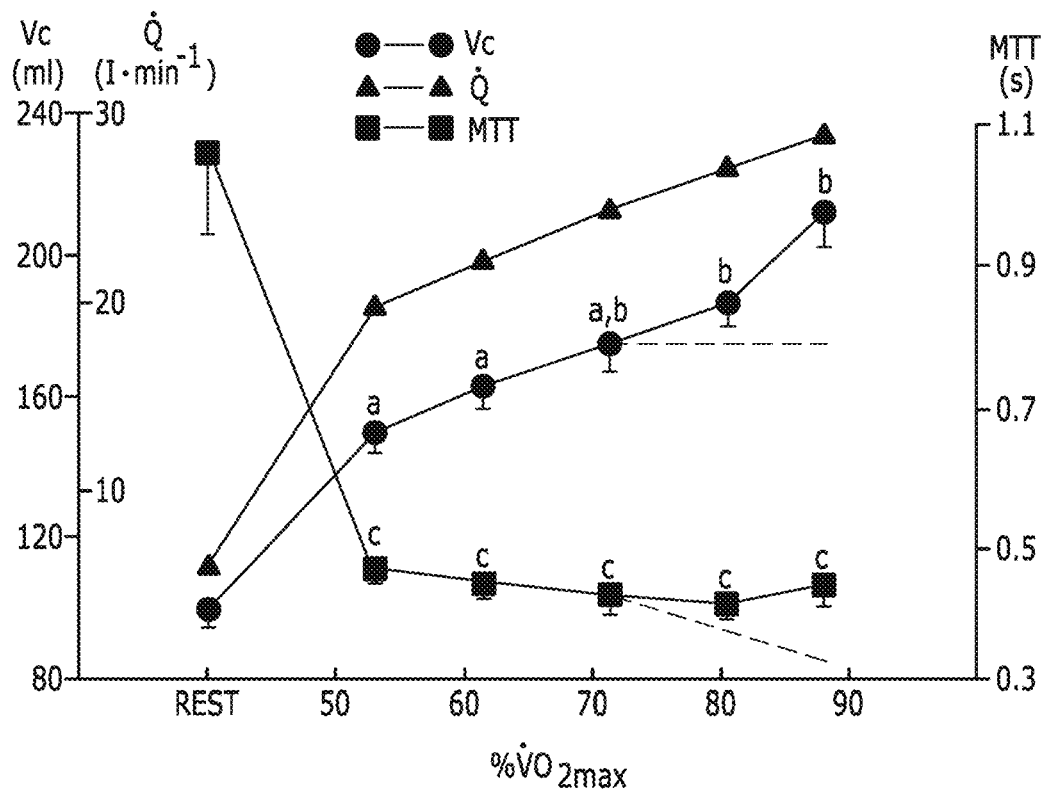
Figure 23B:
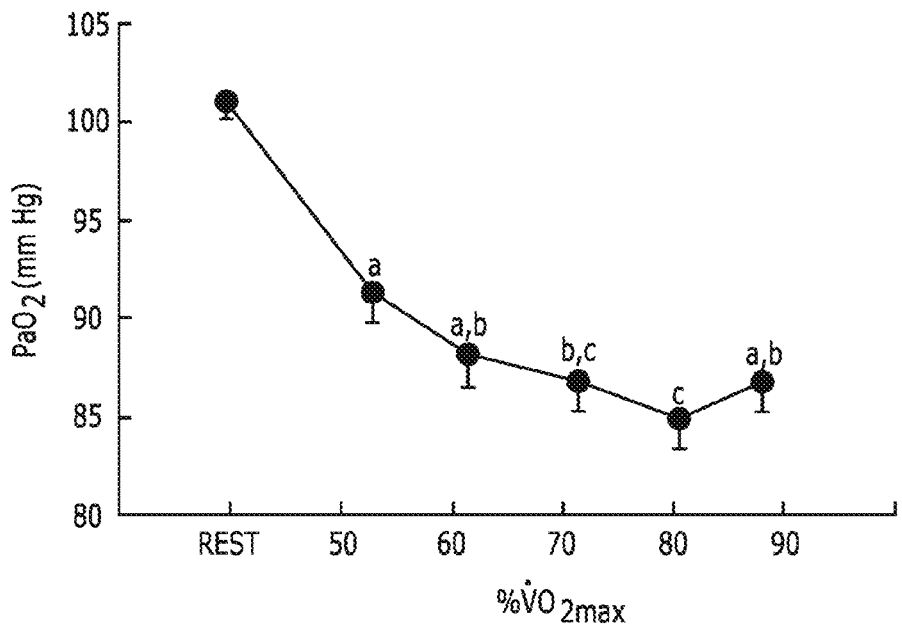
Figure 24A:
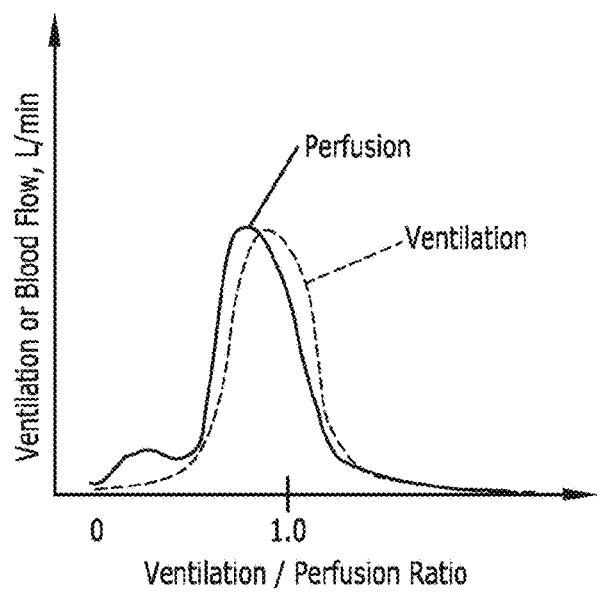
Figure 24B:
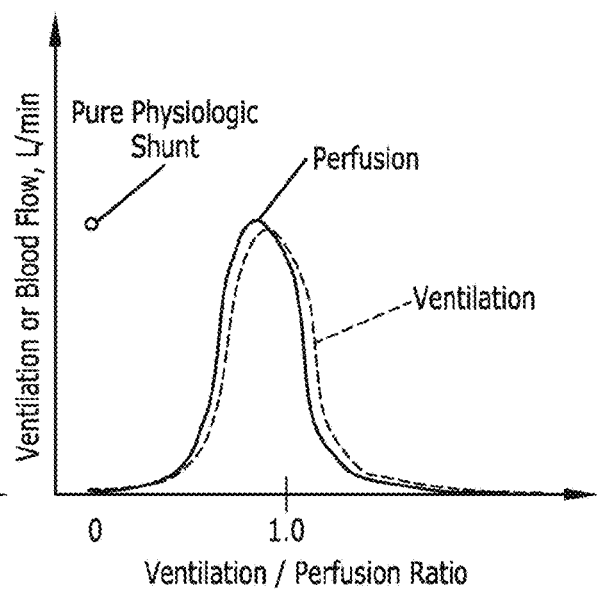
Figure 25:
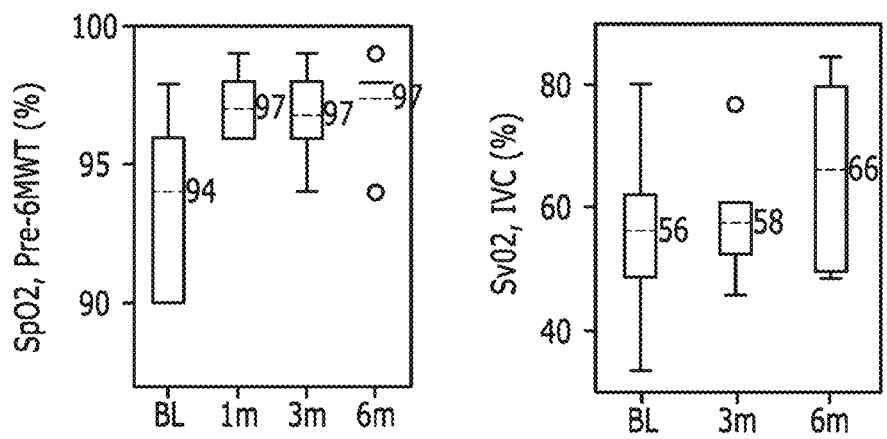
Figure 26:
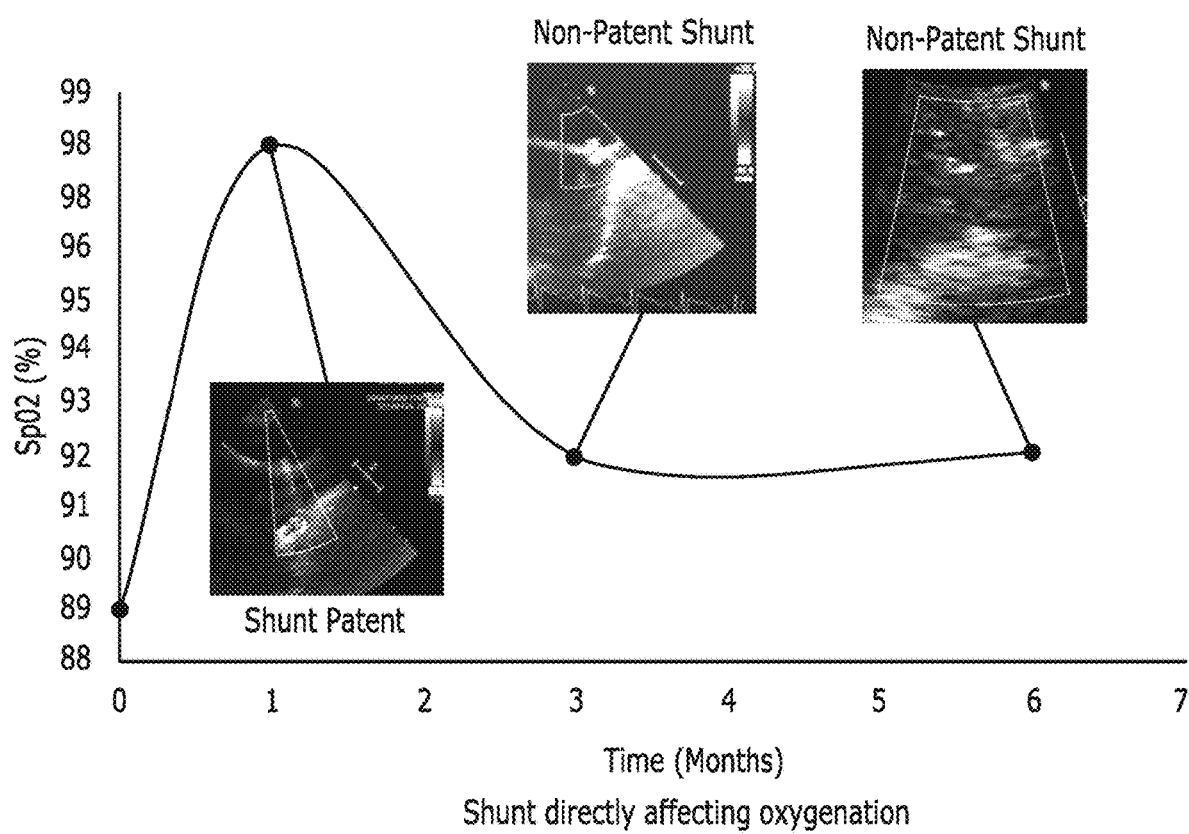

Another embodiment for compliance intervention for treatment of hypoxemia is disclosed in U.S. Pat. No. 10,350,397 (Aria CV), the entirety of which is incorporated by reference. A figure from this patent is reproduced as FIG. 18 which shows digital control of a compliant member for reducing pulsatile pressure. Alternatively, this compliance mechanism can be completely passive.

Pharmacology

In another embodiment of intervention to treat hypoxemia in accordance with the present invention, pharmacology can be used to activate the pressure reduction approach above as well as the approach to affect the trigger mechanism above or both. Drugs will pharmacologically cause pressure reduction through selective vasodilation or by reduction of sympathetic vasoconstriction. In addition, increased transit time can be achieved by prescription of diuretics in pulmonary edema.

The pharmacological agents available to do this include but are not limited to Riociguat, Bosentan, Selexipag, Sildenafil and Iloprost, all prescribed to the patient in a protocol to achieve the improved oxygenation in the protocol discussed above.

Another way to reduce the inappropriate vasoconstriction could be accomplished by stimulating the release atrial natriuretic peptide or other molecules that increase vascular permeability and subsequent reductions in plasma volume[39]. The concentration of these molecules in the bloodstream could be increased via mechanical, electrical, or pharmacologic stimulation from target sites. It is also possible the neprilysin inhibiting pharmaceuticals (i.e. Entresto) could decrease the plasma volume and increase vascular permeability.

Electrical Stimulation

Another embodiment of intervention to treat hypoxemia in accordance with the present invention is the use of electrical stimulation. In this regard, it is known that cardiac stimulation has the ability to modulate the blood pressure of a patient. It is further known that "pacemaker syndrome" could develop, which meant that the patient developed lower cardiac output and lower associated blood pressure.

In this regard, through selective pacing of the right ventricle or the right atrium using patterns known in the art, a reduction in the pressure generated by the right ventricle can be achieved. This would lead to a pressure reduction approach to treating hypoxemia as discussed above. Embodiments to pace the heart to reduce the pressure in accordance with intervention of the present invention are depicted in FIG. 19.

More particularly, FIG. 19 discloses the use of pacing to reduce pressure in the pulmonary artery (PPA) to decrease hypoxemia through a mechanistic increase in red blood cell transit time. Schematic (a) shows a right ventricular/right atrial pacing arrangement. Blood pressure is measured and used to provide feedback/modulation to the pacing algorithm. Schematic (b) shows a theoretical reduction in the pulmonary arterial blood pressure for different pacing algorithms. Schematic (c) shows the Impact of the pacing on the pressure-volume loop of the right ventricle. The right ventricle is placed higher on the pre-load diastolic filling decreases. The decrease in diastolic filling decreases the stroke volume and pulmonary artery pressures by utilizing the Starling mechanism. Schematic (d) shows different pacing algorithms to reduce blood pressure in the pulmonary artery.

Interstitial Fluid Drainage

Another embodiment of intervention for treatment of hypoxemia in accordance with the present invention is interstitial fluid drainage utilizing the lymphatic system or by using pleural drainage devices. Such drainage improves oxygenation by a relief of the compressive pressure of the interstitial space on the pulmonary arterial circulation, thereby decreasing pulmonary vascular resistance. Embodiments useful for this intervention are disclosed in U.S. application Ser. No. 16/541,077 which is hereby incorporated by reference.

Experimental Results

A First-in-Human study was performed to assess the present invention and specifically the performance of a right-to-right shunt positioned at the apposition of the right pulmonary artery and superior vena cava, in patients with WHO Group 1 pulmonary arterial hypertension. A total of 10 patients were enrolled, 9 treated, and 6 completed the study to 6 months follow-up. The baseline characteristics of the patients treated is shown in the Table below:

TABLE 1

Baseline Patient Characteristics

| Characteristic | Average (n = 7) | Range |
| --- | --- | --- |
| Age | 37 | 25-50 |
| Female sex | 4 (57%) | N/A |
| Weight (kg) | 65 | 54-80 |
| PH Group 1 (Idiopathic PAH) | 10 (100%) | N/A |
| NYHA | 3 | 2-3 |
| 6MWD (m) | 241 | 160-337 |
| KCCQ | 38* | 25-58 |
| 5F-36(PCS/MC5) | 36/58 | 14-65/37-83 |
| Borg (Fatigue/Dyspnea) | 2/2 | 0-5 |
| mPAP (mmHg) | 61 | 30-86 |
| mRAP (mmHg) | 9.6 | 5-15 |
| Cardiac Output (L/min) | 5.0 | 4.0-7.7 |
| TAPSE (mm) | 19.6 | 15-25 |
| RA Area (cm$^2$) | 32.6 | 14.1-55.5 |

*This score indicates patients may be more NYHA IV

All had an elevated mean pulmonary artery pressure and displayed signs of symptomatic right heart failure and reduced quality of life. Additionally, due to their disease severity and underlying etiology, some of the patients treated had baseline arterial desaturation (i.e. low oxygen levels in the blood) as measured by peripheral oximetry and SpO2 levels.

After the shunt was implanted, all patients were observed to have an increase in SpO2 from baseline at one month post-procedure, as shown in the graph below:

Interestingly, in one patient, a baseline SpO2 of 89% was observed and an increase in SpO2 to 98% was observed at 1 month at which the shunt was deemed to be patent by echocardiography. At 3 months follow-up, this patient had a confirmed non-patent shunt by echocardiography and SpO2 was reduced to 92%. At 6 months follow-up, the shunt remained closed and the Spo2 levels were similar to those at 3 months. This is shown in the graph below:

These findings show a right-to-right shunt improves arterial oxygenation in patients with baseline desaturation, i.e. hypoxemia.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

1. Quaderi, S. A. & Hurst, J. R. The unmet global burden of COPD. *Glob. Heal. Epidemiol. Genomics* 3, e4 (2018).
2. Hoeper, M. M. et al. A global view of pulmonary hypertension. *Lancet Respir. Med.* 4, 306-322 (2016).
3. Chaouat, A., Naeije, R. & Weitzenblum, E. Pulmonary hypertension in COPD. *Eur. Respir. J.* 32, 1371 LP-1385 (2008).
4. Lacasse, Y., Tan, A.-Y. M., Maltais, F. & Krishnan, J. A. Home Oxygen in Chronic Obstructive Pulmonary Disease. *Am. J. Respir. Crit. Care Med.* 197, 1254-1264 (2018).
5. Currie, G. P. & Douglas, J. G. ABC of chronic obstructive pulmonary disease: Oxygen and inhalers. *BMJ* 333, 34-36 (2006).
6. Committe, G. S. Global Strategy for the Diagnosis, Management, and Prevention of Chronic Obstructive Pulmonary Disease. *Glob. Initiat. Chronic Obstr. Lung Dis.* (2019).
7. Fujimoto, K., Matsuzawa, Y., Yamaguchi, S., Koizumi, T. & Kubo, K. Benefits of Oxygen on Exercise Performance and Pulmonary Hemodynamics in Patients With COPD With Mild Hypoxemia. *Chest* 122, 457-463 (2002).
8. Oba, Y. Cost-effectiveness of long-term oxygen therapy for chronic obstructive disease. *Am. J. Manag. Care* 15, 97-104 (2009).
9. Nishi, S. P. E., Zhang, W., Kuo, Y.-F. & Sharma, G. Oxygen therapy use in older adults with chronic obstructive pulmonary disease. *PLoS One* 10, e0120684-e0120684 (2015).
10. Medical Research Council Working Party. LONG TERM DOMICILIARY OXYGEN THERAPY IN CHRONIC HYPOXIC COR PULMONALE COMPLICATING CHRONIC BRONCHITIS AND EMPHYSEMA: Report of the Medical Research Council Working Party. *Lancet* 317, 681-686 (1981).
11. Alpert, R. A Randomized Trial of Long-Term Oxygen for COPD with Moderate Desaturation. *N. Engl. J. Med.* 375, 1617-1627 (2016).
12. Lacasse, Y., Lecours, R., Pelletier, C., Begin, R. & Maltais, F. Randomised trial of ambulatory oxygen in oxygen-dependent COPD. *Eur. Respir. J.* 25, 1032 LP-1038 (2005).
13. Haskins, S. C. Chapter 15—Hypoxemia. in (eds. Silverstein, D. C. & Hopper, K. B. T.-S. A. C. C. M. (Second E.) 81-86 (W. B. Saunders, 2015). doi:https://doi.org/10.1016/B978-1-4557-0306-7.00015-5
14. Parker, J. A. et al. SNM practice guideline for lung scintigraphy 4.0. *J. Nucl. Med. Technol.* 40, 57-65 (2012).
15. Hwang, H. J. et al. Assessment of Regional Xenon Ventilation, Perfusion, and Ventilation-Perfusion Mismatch Using Dual-Energy Computed Tomography in Chronic Obstructive Pulmonary Disease Patients. *Invest. Radiol.* 51, (2016).
16. Hajian, B. et al. Changes in ventilation-perfusion during and after an COPD exacerbation: an assessment using fluid dynamic modeling. *Int. J. Chron. Obstruct. Pulmon. Dis.* 13, 833-842 (2018).
17. Wagner, P. D. The physiological basis of pulmonary gas exchange: implications for clinical interpretation of arterial blood gases. *Eur. Respir. J.* 45, 227 LP-243 (2015).
18. Levitsky, M. *Pulmonary Physiology*. (2018).
19. Stickland, M. K., Lovering, A. T. & Eldridge, M. W. Exercise-induced arteriovenous intrapulmonary shunting in dogs. *Am. J. Respir. Crit. Care Med.* 176, 300-305 (2007).
20. Petersson, J. & Glenny, R. W. Gas exchange and ventilation-perfusion relationships in the lung. *Eur. Respir. J.* 44, 1023 LP-1041 (2014).
21. Vodoz, J.-F. et al. Right-to-left shunt with hypoxemia in pulmonary hypertension. *BMC Cardiovasc. Disord.* 9, 15 (2009).
22. Sarkar, M., Niranjan, N. & Banyal, P. K. Mechanisms of hypoxemia. *Lung India* 34, 47-60 (2017).
23. Hopkins, S. R. Exercise Induced Arterial Hypoxemia: The role of Ventilation-Perfusion Inequality and Pulmonary Diffusion Limitation BT—Hypoxia and Exercise. in (eds. Roach, R. C., Wagner, P. D. & Hackett, P. H.) 17-30 (Springer US, 2007).
24. WARREN, G. L., CURETON, K. J., MIDDENDORF, W. F., RAY, C. A. & WARREN, J. A. Red blood cell pulmonary capillary transit time during exercise in athletes. *Med. Sci. Sport. Exerc.* 23, (1991).
25. Presson, R. G. et al. Distribution of pulmonary capillary red blood cell transit times. *J. Appl. Physiol.* 79, 382-388 (1995).
26. Jain, S. & Dalvi, B. Atrial septal defect with pulmonary hypertension: When/how can we consider closure? *J. Thorac. Dis.* 10, S2890-S2898 (2018).
27. Holland, A. E. Review series: Aspects of interstitial lung disease: Exercise limitation in interstitial lung disease—mechanisms, significance and therapeutic options. *Chron. Respir. Dis.* 7, 101-111 (2010).
28. Mongardon, N. et al. Epidemiology and outcome of severe pneumococcal pneumonia admitted to intensive care unit: a multicenter study. *Crit. Care* 16, R155-R155 (2012).
29. Powers, K. & Dhamoon, A. Physiology, Pulmonary, Ventilation and Perfusion. *StatPearls* (2019).
30. Ley, S., Kreitner, K.-F., Morgenstern, I., Thelen, M. & Kauczor, H.-U. Bronchopulmonary Shunts in Patients with Chronic Thromboembolic Pulmonary Hypertension: Evaluation with Helical CT and MR Imaging. *Am. J. Roentgenol.* 179, 1209-1215 (2002).
31. Ansari, A. Anatomy and clinical significance of ventricular Thebesian veins. *Clin. Anat.* 14, 102-110 (2001).
32. Laks, M. M., Juratsch, C. E., Garner, D., Beazell, J. & Criley, J. M. Acute Pulmonary Artery Hypertension Produced by Distention of the Main Pulmonary Artery in the Conscious Dog. *Chest* 68, 807-813 (1975).
33. Sonia, V.-R. et al. Increased Sympathetic Nerve Activity in Pulmonary Artery Hypertension. *Circulation* 110, 1308-1312 (2004).
34. Peters, R. M. Coordination of Ventilation and Perfusion. *Ann. Thorac. Surg.* 6, 570-590 (1968).
35. Burrowes, K. S., Clark, A. R. & Tawhai, M. H. Blood flow redistribution and ventilation-perfusion mismatch during embolic pulmonary arterial occlusion. *Pulm. Circ.* 1, 365-376 (2011).
36. Lewis, N. P. et al. Impaired matching of perfusion and ventilation in heart failure detected by 133xenon. *Basic Res. Cardiol.* 91, 45-49 (1996).
37. Murch, S. et al. Pulmonary Hypertension is Associated With Right Ventricular Diastolic Dysfunction. *Hear. Lung Circ.* 22, S58-S59 (2013).
38. Blyth, K. G. et al. Pulmonary arterial pulse pressure and mortality in pulmonary arterial hypertension. *Respir. Med.* 101, 2495-2501 (2007).
39. Curry, F.-R. E. Atrial natriuretic peptide: an essential physiological regulator of transvascular fluid, protein transport, and plasma volume. *J. Clin. Invest.* 115, 1458-1461 (2005).

What is claimed is:

1. A method of treating hypoxemia in a patient comprising:
   conducting oxygen measurements of a patient's blood to establish a baseline oxygen measurement for said patient;
   intervening invasively in the native oxygenation process of said patient so as to increase the oxygen present in said patient's blood;
   said intervening comprising reducing pressure in a pulmonary system of said patient through right-to-right shunting of blood chambers or vessels;
   conducting post-intervention oxygen measurement of said patient's blood after said intervention;
   comparing said post-intervention oxygen measurement with said baseline oxygen measurement to evaluate the efficacy of the intervention.

2. A method according to claim 1, wherein said right-to-right shunting comprises shunting flow from the right pulmonary artery to the superior vena cava.

3. A method according to claim 1, wherein a combination of two or more interventions are performed.

4. A method according to claim 1, further comprising iterating said intervening based on the comparing of said post-intervention oxygen measurement with said baseline oxygen measurement.

5. A method according to claim 4, wherein the iterating of said intervening is repeated until target oxygen measurement is obtained.

6. A system for treating hypoxemia in a patient comprising:
   a device for measuring oxygen levels in a patient;
   a device for intervening invasively in the native pulmonary oxygenation process of a patient, said device comprising a shunting device, wherein said shunting device is an implantable shunt and configured for right-to-right shunting;
   a device for measuring the oxygen levels of said patient post intervention in the native pulmonary oxygenation process of said patient.

7. A system according to claim 6, wherein said implantable shunt is configured for placement in the right pulmonary artery and the superior vena cava of said patient.

8. A method of treating hypoxemia in a patient comprising:
   conducting oxygen measurements of a patient's blood to establish a baseline oxygen measurement for said patient;
   intervening invasively in the native oxygenation process of said patient so as to increase the oxygen present in said patient's blood;
   said intervening comprising restricting flow in a pulmonary system of said patient through placing a flow restriction element into the main pulmonary artery of said patient;
   conducting post-intervention oxygen measurement of said patient's blood after said intervention;
   comparing said post-intervention oxygen measurement with said baseline oxygen measurement to evaluate the efficacy of the intervention.

9. A method of treating hypoxemia in a patient comprising:
   conducting oxygen measurements of a patient's blood to establish a baseline oxygen measurement for said patient;
   intervening invasively in the native oxygenation process of said patient so as to increase the oxygen present in said patient's blood;
   said intervening comprising reducing pressure in a pulmonary circulation by introducing compliance into said pulmonary circulation by placing a gas-filled balloon into the pulmonary circulation;
   conducting post-intervention oxygen measurement of said patient's blood after said intervention;
   comparing said post-intervention oxygen measurement with said baseline oxygen measurement to evaluate the efficacy of the intervention.

10. A method according to claim 9, wherein said balloon is disposed in the SVC.

11. A method of treating hypoxemia in a patient comprising:
    conducting oxygen measurements of a patient's blood to establish a baseline oxygen measurement for said patient;
    intervening invasively in the native oxygenation process of said patient so as to increase the oxygen present in said patient's blood;
    said intervening comprising reducing pressure in a pulmonary circulation by draining the lymphatic system; wherein draining the lymphatic system includes draining the interstitial spaces of said lymphatic system;
    conducting post-intervention oxygen measurement of said patient's blood after said intervention;
    comparing said post-intervention oxygen measurement with said baseline oxygen measurement to evaluate the efficacy of the intervention.

12. A system for treating hypoxemia in a patient comprising:
    a device for measuring oxygen levels in a patient;
    a device for intervening invasively in the native pulmonary oxygenation process of a patient, said device comprising a flow restriction element configured for placement into the main pulmonary artery of said patient;
    a device for measuring the oxygen levels of said patient post intervention in the native pulmonary oxygenation process of said patient.

13. A system for treating hypoxemia in a patient comprising:
    a device for measuring oxygen levels in a patient;
    a device for intervening invasively in the native pulmonary oxygenation process of a patient, said device comprising a compliance device in the form of a gas-filled balloon configured for placement in the pulmonary circulation;
    a device for measuring the oxygen levels of said patient post intervention in the native pulmonary oxygenation process of said patient.

14. A system for treating hypoxemia in a patient comprising:
    a device for measuring oxygen levels in a patient;
    a device for intervening invasively in the native pulmonary oxygenation process of a patient, said device comprising a lymphatic drainage device configured to drain the interstitial spaces of said lymphatic system;
    a device for measuring the oxygen levels of said patient post intervention in the native pulmonary oxygenation process of said patient.

* * * * *